United States Patent
Goldman et al.

(10) Patent No.: US 11,224,502 B2
(45) Date of Patent: Jan. 18, 2022

(54) URETERAL STENTS AND METHODS OF USING THE SAME

(71) Applicant: C.R. BARD, INC., Murray Hill, NJ (US)

(72) Inventors: David Matthew Goldman, Decatur, GA (US); Peter Curry, Decatur, GA (US); Joseph Anthony Urban, Atlanta, GA (US); Jeremy M. Wiste, Stewartville, MN (US)

(73) Assignee: C.R. BARD, INC., Murray Hill, NJ (US)

( * ) Notice: Subject to any disclaimer, the term of this patent is extended or adjusted under 35 U.S.C. 154(b) by 578 days.

(21) Appl. No.: 16/067,928

(22) PCT Filed: Jan. 5, 2017

(86) PCT No.: PCT/US2017/012328
§ 371 (c)(1),
(2) Date: Jul. 3, 2018

(87) PCT Pub. No.: WO2017/120332
PCT Pub. Date: Jul. 13, 2017

(65) Prior Publication Data
US 2021/0015597 A1   Jan. 21, 2021

Related U.S. Application Data

(60) Provisional application No. 62/276,521, filed on Jan. 8, 2016.

(51) Int. Cl.
*A61F 2/04* (2013.01)

(52) U.S. Cl.
CPC .......... *A61F 2/04* (2013.01); *A61F 2002/047* (2013.01)

(58) Field of Classification Search
CPC ....... A61M 25/04; A61M 25/09; A61F 2/848; A61F 2/958
See application file for complete search history.

(56) References Cited

U.S. PATENT DOCUMENTS

| 2004/0193092 A1 | 9/2004 | Deal et al. |
| 2006/0015190 A1 | 1/2006 | Robertson |

FOREIGN PATENT DOCUMENTS

| CA | 2945515 A1 | 10/2015 |

OTHER PUBLICATIONS

International Search Report and Written Opinion from International Application No. PCT/US2017/012328 dated Apr. 14, 2017.
U.S. Appl. No. 62/276,521, filed Jan. 8, 2016.

*Primary Examiner* — Yashita Sharma
(74) *Attorney, Agent, or Firm* — Marcus S. Simon

(57) ABSTRACT

Embodiments disclosed herein relate to ureteral stents having an elongated stent body and one or more deformable bladders secured thereto, and methods of using the same.

16 Claims, 12 Drawing Sheets

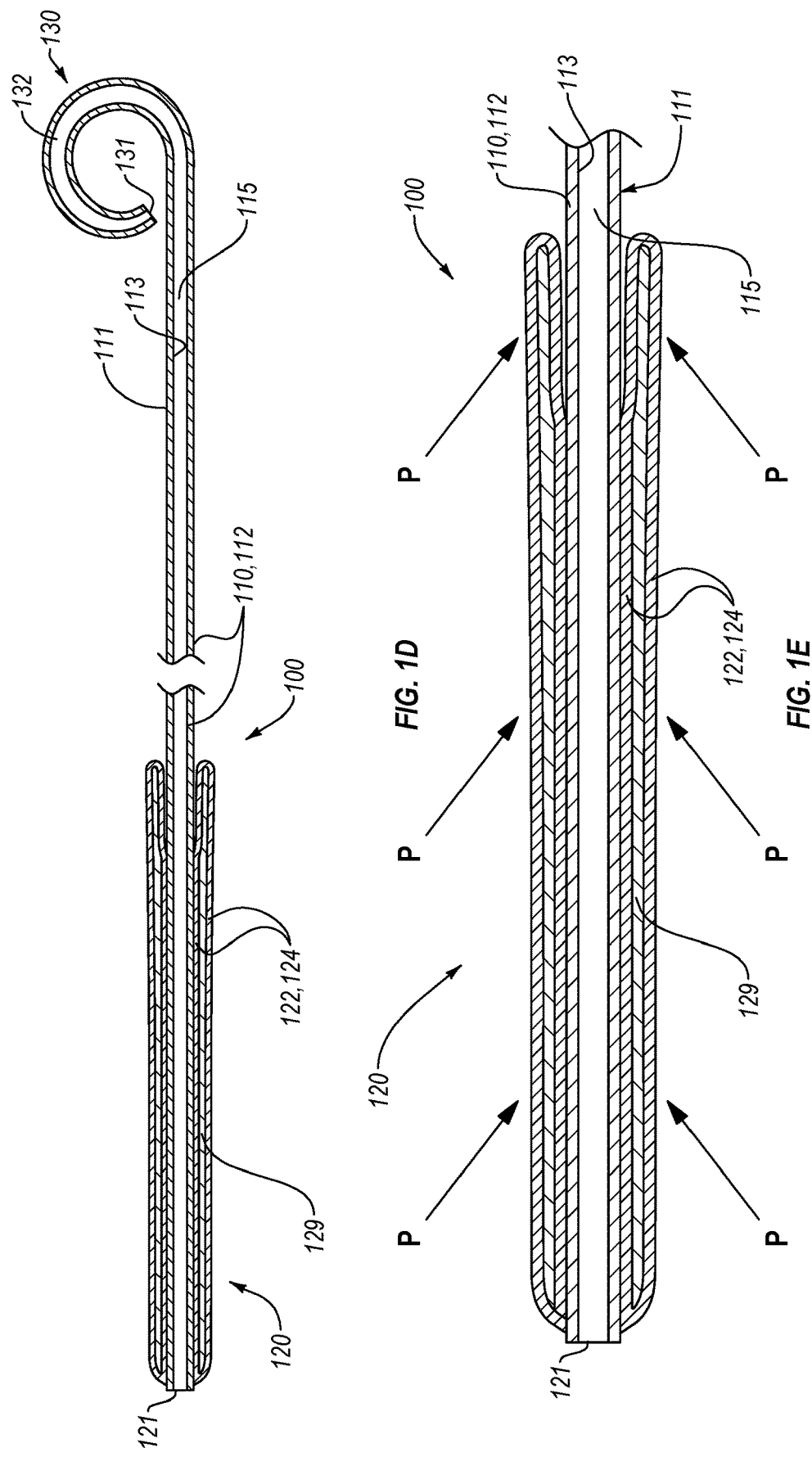

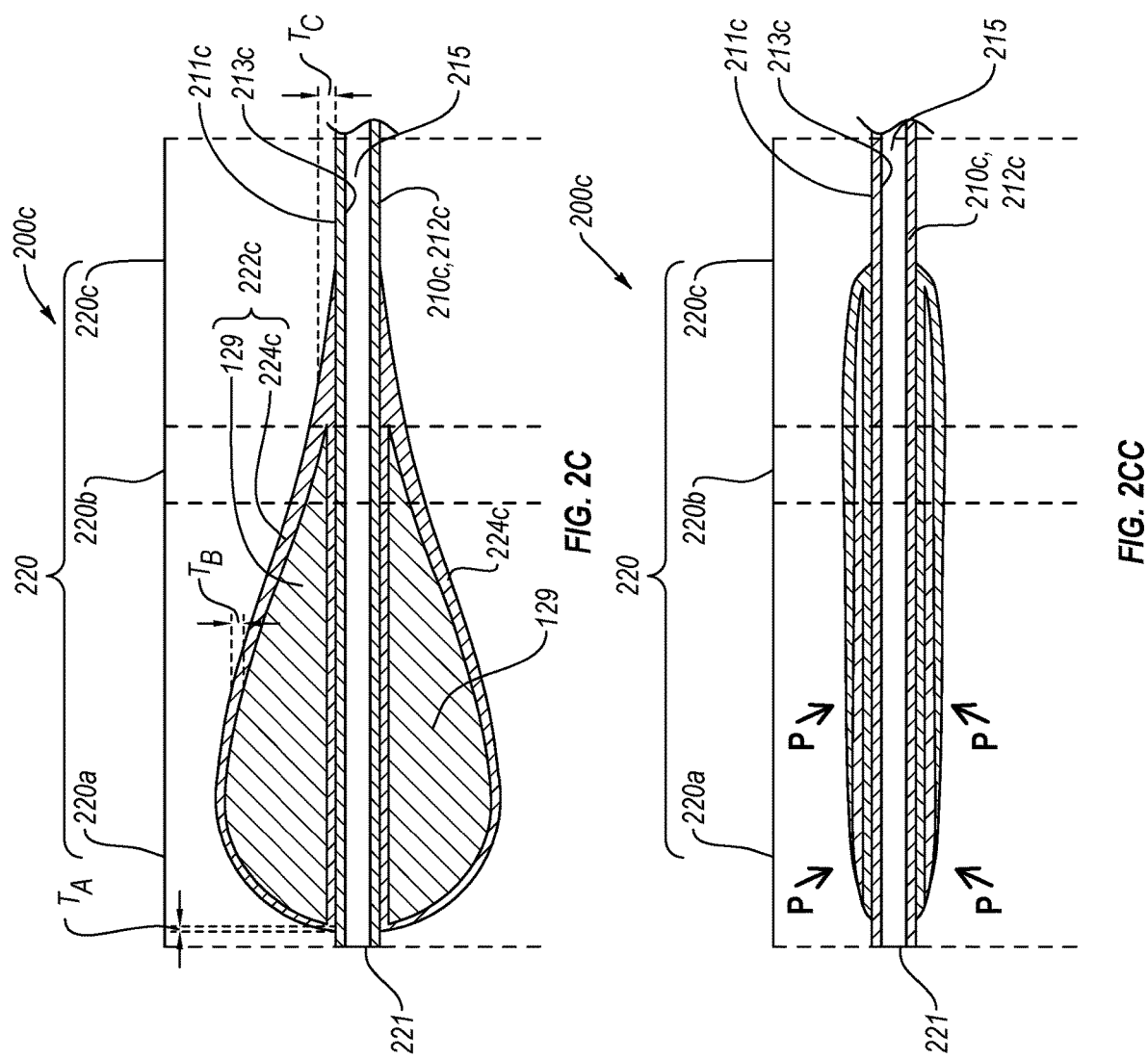

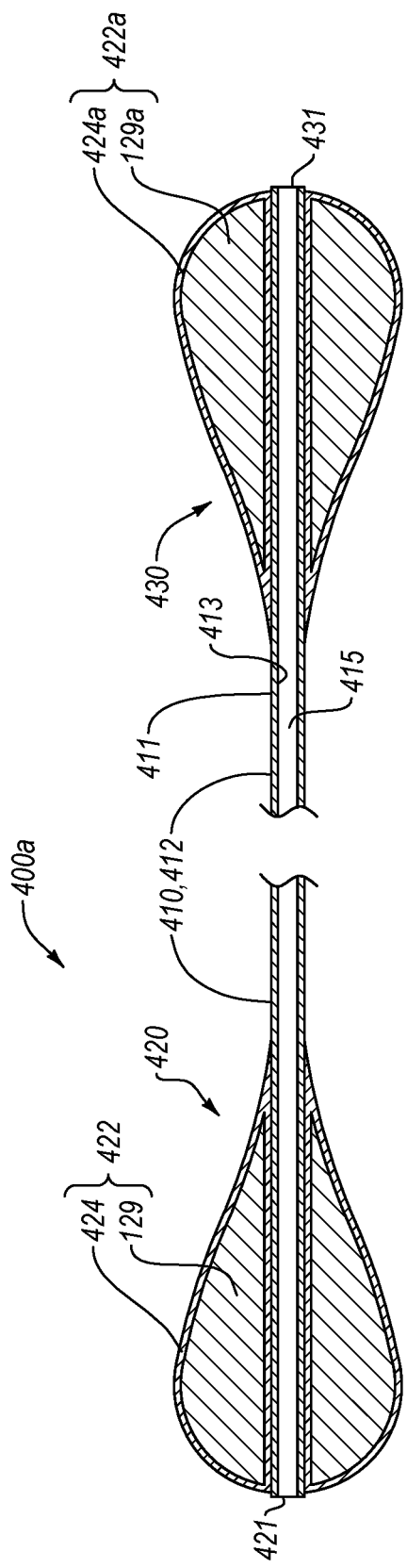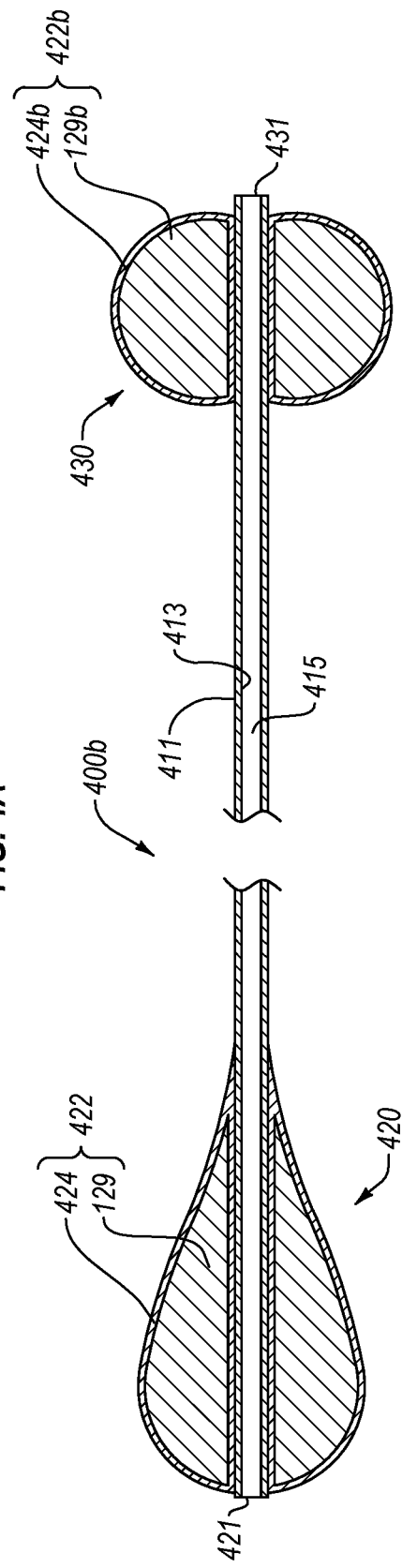
FIG. 4A
FIG. 4B

URETERAL STENTS AND METHODS OF USING THE SAME

CROSS-REFERENCE TO RELATED APPLICATIONS

This application claims priority to U.S. Provisional Application 62/276,521 filed on 8 Jan. 2016, the disclosure of which is incorporated herein, in its entirety, by this reference.

BACKGROUND

Catheterization is a relatively common medical procedure for draining fluid from a patient. In the case of ureteral catheterization, a ureteral stent and/or a catheter may prevent or treat an obstruction affecting urine flow from the kidney to the bladder. In most cases, stents restore the free flow of urine from the kidney. In some instances, catheterization may also facilitate injection of liquids into the kidney. Typically, ureteral catheterization is performed by inserting a stent through a patient's urethra, bladder, ureter, and into the kidney so that one end of the stent is in the bladder and the other end is in the kidney.

Stents can be used to prevent closure of a passage, tube, or duct. The diameter of a stent lumen can be expanded after being positioned within the patient, or they can be self-expanding such as in response to a change in temperature. In most cases, stents are designed to maintain their lumen diameter after deployment and positioning. Stents may be placed within a sheath for deployment. After deployment, the stent is designed to remain in the deployed configuration.

Stents are often used to prevent closure or obstruction of the ureter. In some cases, the ureter may be blocked, for example, by a kidney stone. While opening the ureter to allow resolution of a kidney stone may require only temporary positioning of the stent (days or weeks), other conditions may require the stent to remain in the ureter for longer periods of time, such as several months or longer. In some cases, stents may be placed within the ureter to prevent spasms and/or collapse of the ureter after an operation, such as after kidney stone removal.

Guidewires may be used to position a stent. In some cases, a guidewire may be inserted into the ureter. The stent may be positioned about the guidewire and advanced until the stent is properly positioned. In some cases, a cystoscope may aid in positioning the guidewire. In many cases, fluoroscopy may be used to help ensure proper placement of the guidewire prior to advancing the stent.

In some cases, a stent may move after being positioned in the ureter. For example, the stent may move towards the kidney or bladder. Movement of the stent may arise for various reasons. For example, movement of the stent may be caused by routine activity and/or from strenuous physical activity by the patient. Movement of the stent may cause the ureter to partially collapse in regions of the ureter vacated by the stent and/or the stent to irritate or damage the bladder (e.g. the trigone) or kidney.

In order to prevent or reduce movement of a stent or (maintain patency), one or both ends of the stent may be curled in a pigtail, spiral, or J-shape (i.e., a curled retaining structure). The curled retaining structure may prevent or reduce migration of the stent within the ureter. Stents having a curled retaining structure at the kidney end of the stent (e.g., proximal end) may prevent the stent from moving towards the bladder. A curled retaining structure positioned at the bladder end of the stent (e.g., distal end) may prevent movement of the stent towards the kidney. Additionally, structures at the bladder end of the (e.g., a coil, string) may also aid in retrieval and removal of the stent.

Stents may cause or contribute to patient discomfort and pain. For example, patient discomfort and pain may be attributed to the stent irritating the trigone area of the bladder. Irritation of the trigone may occur when the stent or a retaining structure (e.g. curl retaining structure), contacts the trigone. The trigone (or trigonum) is a triangular-shaped region located on the floor of the urinary bladder, and is roughly defined by the opening of the urethra and the two ureteral orifices. The trigone is believed to be particularly innervated and, therefore, is especially sensitive to irritation caused by pressure, such as contact with a stent.

In some cases, stents may result in urine reflux. Urine reflux may occur when urine travels from the bladder to the kidneys in response to retrograde pressure. Retrograde pressure occurs in the bladder when attempting to void the bladder of urine, and may transmit urine or other fluids up the stent to the kidney. In response to this pressure, the lower portion of the ureter, proximal the bladder, normally closes during routine voiding of the bladder, but the presence of a stent or catheter may interfere with this closure. This may lead to irritation of the ureter as well as urine reflux.

SUMMARY

Embodiments disclosed herein include a ureteral stent having an elongated stent body, one or more deformable bladders secured thereto, and methods for utilizing the same. Each of the one or more deformable bladders may be secured to an end region of an elongated stent body of the ureteral stent. The one or more deformable bladders may serve to secure the stent within a ureter, reduce movement of the stent within the ureter, improve comfort of the stent in the bladder (e.g., the trigone) of the subject, aid in insertion and/or retrieval of the ureteral stent from the ureter, or combinations of the foregoing.

In an embodiment a ureteral stent is disclosed. The ureteral stent includes an elongated stent body including a proximal end region including a first retaining structure, with the proximal end region configured for positioning in a kidney. The elongated stent body further includes a distal end region configured for positioning in a bladder and spaced longitudinally from the proximal end region. The elongated stent body also includes an outer surface and an inner surface defining a lumen extending between the proximal end region and the distal end region of the elongated stent body. The ureteral stent includes a deformable bladder secured to and surrounding at least a portion of the distal end region of the elongated stent body. The deformable bladder includes a resiliently deformable envelope that is imperforately sealed and an inert fluid sealed within the resiliently deformable envelope.

In an embodiment, a method of inserting a ureteral stent into a ureter of a subject is disclosed. The ureteral stent as disclosed above is provided. The method includes placing the resiliently deformable bladder in a delivery position by positioning a delivery sheath over the resiliently deformable bladder and the elongated stent body, thereby causing the resiliently deformable bladder to flatten over a larger length of the elongated stent body than when in an deployed position. The method includes inserting the ureteral stent placed in the delivery sheath into the ureter via the bladder of the subject. The method includes, after the ureteral stent placed in the delivery sheath is inserted into the ureter, positioning the ureteral stent in the subject such that the proximal end region is positioned in the kidney of the subject and the distal end region is positioned in the bladder of the subject. The method includes expanding the resiliently deformable bladder to the deployed position by withdrawing the delivery sheath from the ureteral stent.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

FIGS. 1B-1E are side cross-sectional views of the ureteral stent of FIG. 1A, in various deployed and delivery configurations.

FIGS. 2A-2D are side cross-sectional views of portions of ureteral stents according to embodiments.

FIGS. 4A and 4B are side cross-sectional views of ureteral stents according to embodiments.

DETAILED DESCRIPTION

Embodiments disclosed herein include a ureteral stent having an elongated stent body, one or more deformable bladders secured thereto, and methods for utilizing the same. Each of the one or more deformable bladders may be secured to an end region of an elongated stent body of the ureteral stent. The one or more deformable bladders may serve to secure the stent within a ureter, reduce movement of the stent within the ureter, improve comfort of the stent in the bladder (e.g., the trigone) of the subject, aid in insertion and/or retrieval of the ureteral stent from the ureter, or combinations of the foregoing.

Figure 1A:
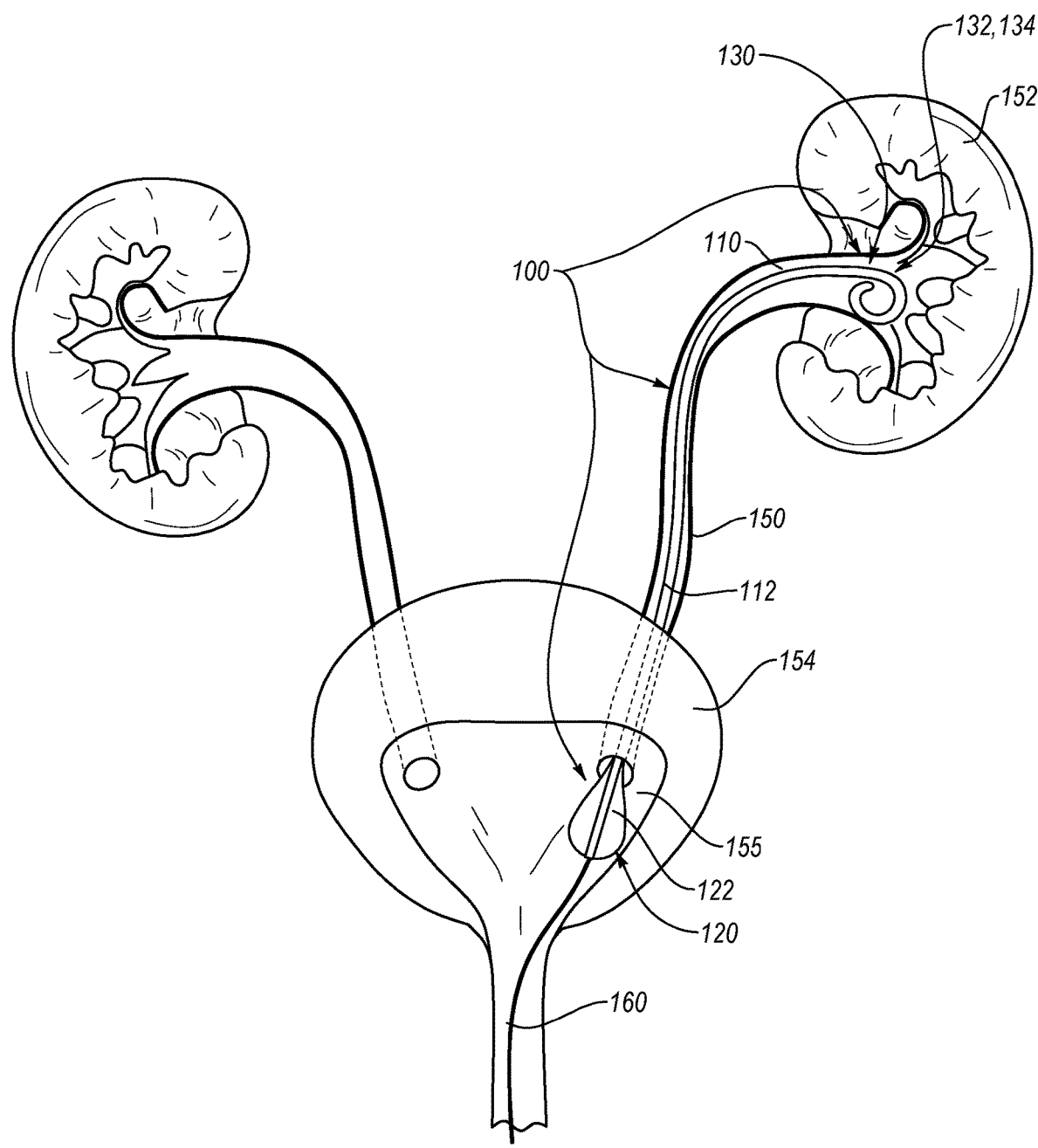
FIG. 1A is a schematic of a ureteral stent disposed in a ureter of a subject, according to an embodiment.
Figure 1B:
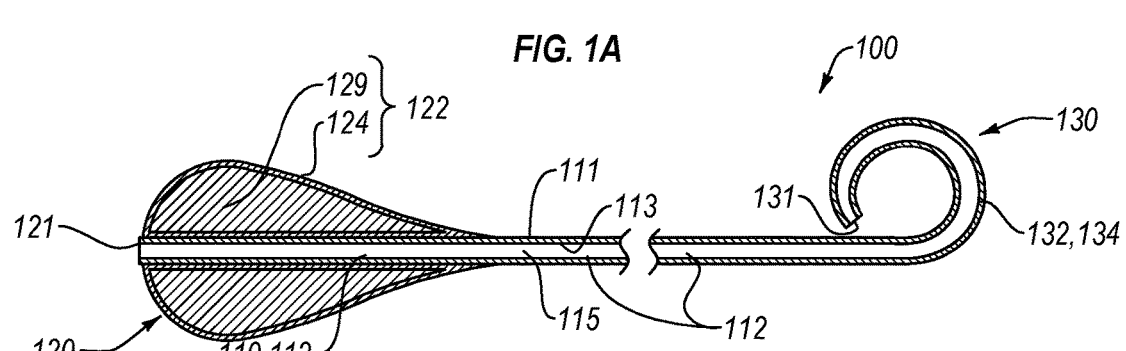

FIGS. 1A and 1B are a schematic illustration and a side cross-sectional view, respectively, of a ureteral stent 100 positioned in a ureter 150 of a subject. The ureteral stent 100 includes an elongated stent body 110 having a distal end region 120 (e.g., the end region farthest from the heart of the subject) longitudinally spaced from a proximal end region 130. The elongated stent body 110 includes at least one sidewall 112 having an outer surface 111 and an inner surface 113. The inner surface defines a lumen 115 that extends completely through the elongated stent body 110 from a distal end 121 of the distal end region 120 to a proximal end 131 of the proximal end region 130. The lumen 115 allows fluid communication between the distal end 121 of the distal end region 120 and the proximal end 131 of the proximal end region 130. The lumen 115 terminates at the proximal end 131 and the distal end 121 of the elongated stent body 110. The distal end 121 and the proximal end 131 may include one or more openings formed therein. The ureteral stent 100 includes one or more retaining structures, with the retaining structures being configured to cause a portion of the ureteral stent 100 to substantially remain in position relative to an anatomical feature of a subject.

The ureteral stent 100 includes a first retaining structure 132 at the proximal end region 130. The first retaining structure 132 is configured to cause the proximal end region 130 to remain in position in a kidney 152 of the subject, such as proximate to the ureteral orifice therein. For example, the first retaining structure 132 may be a coil 134 of the elongated stent body 110 at the proximal end region 130. The ureteral stent 100 further includes a deformable bladder 122 located at the distal end region 120. The deformable bladder 122 acts as a second retaining structure positioned adjacent to or in the bladder 154.

The deformable bladder 122 includes a fluid tight, resiliently deformable envelope 124 secured to the outer surface 111 of the elongated stent body 110 at or adjacent to the distal end region 120 thereof. The resiliently deformable envelope 124 may at least partially surround at least a portion of the outer surface 111, such as being secured around the outer surface 111 of the elongated stent body 110 (e.g., secured 360 degrees around a region of the outer surface 111). The resiliently deformable envelope 124 at least partially defines a cavity in which an inert fluid 129 is disposed, such as entirely internal to the resiliently deformable envelope 124 and/or between the resiliently deformable envelope 124 and the outer surface 111. The cavity retains the inert fluid 129 therein. As explained in more detail below, the resiliently deformable envelope 124 may be constructed of one or more materials capable of resiliently deforming along the elongated stent body 110. The deformable bladder 122 and resiliently deformable envelope 124 may be substantially imperforate, such as having a substantially smooth exterior surface and/or having no filling ports therein. For example, the resiliently deformable envelope 124 may include a substantially smooth, continuous outer and inner surface having the inert fluid 129 sealed therein prior to use, such as during manufacturing. The inert fluid 129 may be retained within the resiliently deformable envelope 124 and/or between the resiliently deformable envelope 124 and the at least one sidewall 112. Stated another way, the inert fluid 129 may be completely internal to the resiliently deformable envelope 124 (e.g., sealed therein). In an embodiment, the resiliently deformable envelope 124 includes silicone and the inert fluid includes mineral oil sealingly contained within the resiliently deformable envelope 124 prior to insertion into a subject, with the resiliently deformable envelope 124 exhibiting a surface free of discontinuities such as a filling port.

In some embodiments, the resiliently deformable envelope 124 may be a self-contained, sealed vessel having the inert fluid 129 sealed therein prior to deployment. For example, the resiliently deformable envelope 124 may be substantially toroidal (e.g., a substantially donut shaped tube) having one or more (longitudinal) cross-sectional shapes, such as a tear drop shape with a lumen extending therethrough. The resiliently deformable envelope 124 may be imperforate (e.g., having no filling ports therein), and the inert fluid 129 may be present therein prior to deployment in a subject. For example, the deformable bladder 122 may include a (elastomeric) silicone resiliently deformable envelope 124 having a mineral oil inert fluid 129 imperforately sealed therein. In some embodiments, the prefilled deformable bladders herein may be ready for delivery and deployment into a subject without adding (e.g., any or more) inert fluid into the deformable bladder prior to or during deployment.

The inert fluid 129 may be entirely contained (e.g., sealed) within the resiliently deformable envelope 124 between an innermost wall and an outermost wall of the (toroidal) resiliently deformable envelope, such that the elongated stent body 110 does not contact the inert fluid 129. In such embodiments, the innermost wall of the toroidal resiliently deformable envelope may be secured to the outer surface 111 of the elongated stent body 110, and the outermost wall of the toroid may contact the subject. It should be understood that the innermost and outermost wall of the toroidal resiliently deformable envelopes herein may be substantially a singular continuous surface, and the use of the terms innermost and outermost merely delineate the portions of the toroid facing radially outward and radially inward (outside and inside of donut, respectively). In some embodiments, the resiliently deformable envelope 124 may be secured to the outer surface 111 only at a distal portion (e.g., segment), a medial portion, or a proximal portion of the distal end region 120, such that the resiliently deformable envelope 124 can freely move (e.g., slide) longitudinally up or down the elongated stent body 110 relative to the secured portion.

In some embodiments and as explained in more detail below (FIGS. 3B and 3F), a resiliently deformable envelope may not be toroidal. Rather, the resiliently deformable envelope may be a single layer of resiliently deformable envelope material secured to the elongated stent body, thereby forming an imperforate sealed cavity (having no filling ports therein) between the resiliently deformable envelope material and the elongated stent body.

During deployment, the resiliently deformable envelope 124 may be deformed from a deployed position to stretch (e.g., longitudinally) along the elongated stent body 110, thereby reducing cross-sectional dimension(s) (e.g., radial dimensions) as a function of longitudinal displacement. Put another way, as the deformable bladder 122 is pushed or otherwise stretched along the outer surface 111 of the elongated stent body 110 toward the midpoint of the elongated stent body 110, the lateral dimension(s) of the deformable bladder 122 decreases. Such a configuration may provide a comfortable ureteral stent capable of being inserted into position without the need of filling the deformable bladder 122 with a fluid after deployment. The embodiments disclosed herein may also provide a sufficiently soft interface between the subject and the ureteral stent to reduce or eliminate discomfort to the subject, such as from a portion of the elongated stent body contacting the trigone 155.

In some embodiments, the ureteral stent 100 may include a retrieval line 160 coupled thereto. The retrieval line 160 may be configured to facilitate deployment and/or removal of the ureteral stent 100. For example, the retrieval line 160 may be a line (e.g., cord, string, tether, etc.) secured to a portion (e.g., the distal end region 120) of the ureteral stent 100, such that the ureteral stent 100 may be removed from the subject by pulling on the retrieval line 160.

Figure 1C:
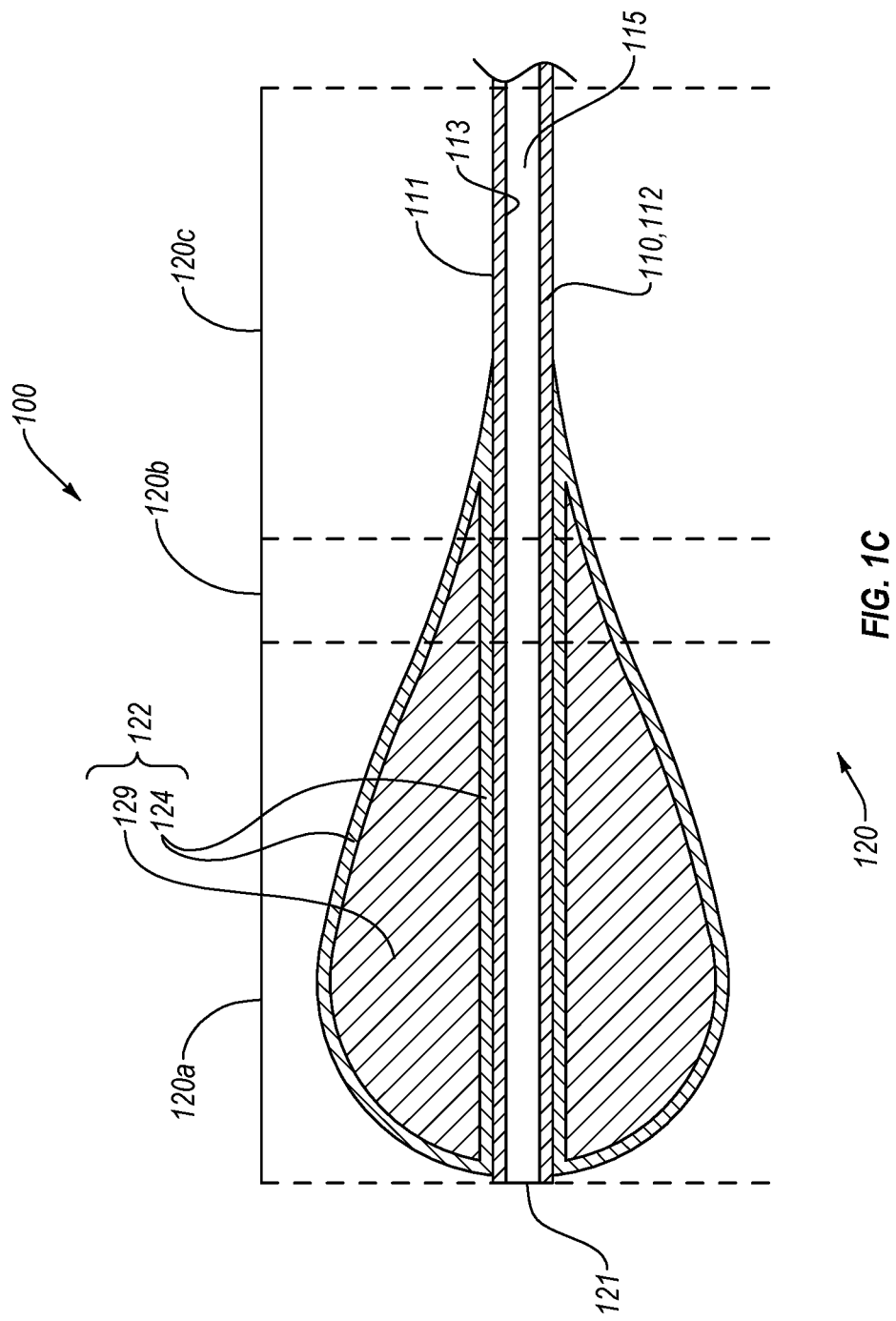

FIG. 1C is a cross-sectional view of a portion of the ureteral stent 100 depicted in FIG. 1B. The deformable bladder 122 may have a deployed shape when the resiliently deformable envelope 124 does not have sufficient pressure applied thereto to deform the deformable bladder 122. For example, the deformable bladder 122 may have a substantially teardrop longitudinal cross-section when in a deployed configuration. Responsive to pressure applied to the resiliently deformable envelope 124, the resiliently deformable envelope 124 and inert fluid 129 therein may deform from the deployed shape to comply with the pressure applied thereto. For example, upon application of an external pressure (e.g., due to pressure exerted thereon in a bladder, kidney, etc.), the deformable bladder 122 may deform to a substantially flattened shape. In an embodiment, the deformable bladder 122 may be configured with a circumferential teardrop shape and, upon positioning in the bladder 154 of the subject; the teardrop shape may become substantially flattened in one or more dimensions due to compliance with pressures exerted thereon by the adjacent anatomical structure(s) of the subject.

The resiliently deformable envelope 124 may be constructed of a material capable of resilient deformation. The resiliently deformable envelope 124 may include a material having a modulus of elasticity and dimensions sufficient to allow the deformable bladder 122 to elongate along a portion of the outer surface 111 of the elongated stent body 110 and reduce (radial) cross-sectional dimensions, responsive to external pressure applied thereto. For example, the resiliently deformable envelope 124 may include or be formed of an elastomer of one or more of silicone rubber, natural rubber, natural polyisoprene, synthetic polyisoprene, polyurethane, nylon, or nitrile. The wall of the resiliently deformable envelope 124 may include one or more different thicknesses, each configured to suit one or more of the particular subject's anatomy, deployment position in the subject, or expected external pressures applied thereto. The thickness of the resiliently deformable envelope 124 may be selected to provide one or more of a desired level of compliance to the deformable bladder 122 responsive to pressure thereon, resilience by the deformable bladder 122, or comfort when the ureteral stent 100 having the deformable bladder 122 is positioned in the subject. For example, a suitable wall thickness of the resiliently deformable envelope 124, in a deployed configuration, may be about 50 µm or more, such as about 50 µm to about 3 mm, about 250 µm to about 2 mm, about 300 µm to about 1 cm, about 50 µm to about 750 µm, about 500 µm to about 1.5 mm, about 500 µm, or less than about 3 mm.

The inert fluid 129 in the deformable bladder 122 may include any fluid that is relatively inert (e.g., non-toxic) in the body of the subject and is fluid at the internal body temperature of the subject. For example, the inert fluid 129 may include one or more oils, such as mineral oil, a nut oil (e.g., almond oil), a cold-pressed vegetable oil, a seed oil, coconut oil, olive oil, or any other oil that is non-toxic to a human subject. In some embodiments, the inert fluid 129 may include saline or deionized water. In some embodiments, the inert fluid 129 may be a mixture of one or more oils, saline, or deionized water. The inert fluid 129 may be present in the resiliently deformable envelope 124 in an amount sufficient to allow the deformable bladder 122 to deform along the elongated stent body 110 for insertion and provide a sufficiently compliant deformable bladder 122 when in a deployed configuration to sit comfortably in the bladder (e.g., trigone) or other portion of the subject. For example, the resiliently deformable envelope 124 may contain about 0.25 cc or more of the inert fluid 129, such as about 0.25 cc to about 10 cc, about 0.5 cc to about 5 cc, about 0.25 cc to about 2 cc, about 1 cc to about 3 cc, about 2 cc to about 4 cc, about 3 cc to about 6 cc, or less than about 6 cc of the inert fluid 129.

As shown in FIG. 1C, the resiliently deformable envelope 124 may be secured to the elongated stent body 110. The resiliently deformable envelope 124 may have a first end secured to the elongated stent body 110 at a more distal portion the distal end region 120 of the elongated stent body 110 and a second end secured to the elongated stent body 110 at a more proximal portion of the distal end region 120 (e.g., a position closer to the midpoint of the elongated stent body 110). One or more portions (e.g., the first and second ends) of the resiliently deformable envelope 124 may be secured to the elongated stent body 110 by one or more of an adhesive (e.g., an epoxy), integral formation (e.g., fit in or on one or more flanges formed on the elongated stent body 110), interference fit, one or more retainers (e.g., clamps, clips, etc.), or any other means of securing the resiliently deformable envelope 124 to the elongated stent body 110.

As shown in FIG. 1C, the ureteral stent 100 may be sized and configured to position and retain one or more specific portions thereof adjacent to one or more anatomical features in the subject. The more proximal segment 120c of the distal end region 120 may be configured to rest in the ureter of a subject. The more medial portion 120b of the distal end region 120 may be configured to be positioned in the ureteral orifice in the bladder. The most distal segment 120a of the distal end region 120 may be configured to rest in the bladder of the subject, such as adjacent to or on the trigone of the subject. In some embodiments, the distal end 121 of the elongated stent body 110 may protrude past the deformable bladder 122, or may be coextensive or recessed therein. The length of the elongated stent body 110 may be configured to provide a selected fit of the deformable bladder 122 and the first retaining structure, respectively, in the bladder 154 and kidney 152 (FIG. 1A) of a subject and provide fluid communication therebetween. The length of the elongated stent body 110 may be about 6 cm or more, such as about 6 cm to about 40 cm, about 10 cm to about 20 cm, about 15 cm to about 30 cm, about 20 cm to about 25 cm, about 10 cm to about 25 cm, or less than about 30 cm. The width (e.g., diameter) of the elongated stent body 110 (as measured from the outer surface 111) may be about 1 mm or more, such as about 1 mm to about 5 mm, about 1.25 mm to about 2 mm, about 1.5 mm to about 2.5 mm, about 2 mm to about 3 mm, about 2.5 mm to about 4 mm, about 3 mm to about 5 mm, or less than about 5 mm.

The elongated stent body 110 may be constructed of or include thereon biocompatible plastics or polymers. For example, the elongated stent body 110 may be formed from ethylene vinyl acetate (EVA), polytetrafluoroethylene (PTFE), silicone polyurethane, a polyamide, polyurethane plastics, polyethylene plastics, any other suitable thermoplastics or block copolymers thereof, or combinations including any of the foregoing. In an embodiment, the elongated stent body 110 may be constructed of or include a metallic material such as stainless steel. In an embodiment, the elongated stent body 110 may be constructed of or include a superelastic or shape memory material. For example, a nickel-titanium alloy (e.g., nitinol) is a suitable superelastic or shape memory alloy for the elongated stent body 110. In an embodiment, at least a portion of the outer surface 111 of the elongated stent body 110 may be coated with any of the foregoing materials. For example, one or more portions of the inner surface 113 and/or the outer surface 111 of the elongated stent body 110 may be coated with a biocompatible polymer.

FIGS. 1D and 1E are cross-sectional views of the ureteral stent 100 of FIGS. 1A-1C with the deformable bladder 122 in a delivery configuration (e.g., at least partially deformed and/or at least partially collapsed configuration) suitable for implantation in a subject, with FIG. 1E being a close-up view a portion of FIG. 1D. The deformable bladder 122 may be deformed (e.g., placed in a delivery configuration) responsive to an external pressure P applied thereto. For example, inward pressure P directed toward the midpoint of the elongated stent body 110 may cause the resiliently deformable envelope 124 to compress inward toward the elongated stent body 110 and along the elongated stent body 110 toward the midpoint thereof. Such deformation may correspondingly reduce the lateral/radial (looking down the longitudinal axis) cross-sectional dimension(s) of the deformable bladder 122. During deformation, the inert fluid 129 remains in the resiliently deformable envelope 124 and displaces therein to comply with the change in shape of the resiliently deformable envelope 124 responsive to the pressure P.

In some embodiments, the greatest outer dimension of the ureteral stent 100 (e.g., outer dimension of the resiliently deformable envelope 124) with the deformable bladder 122 in a deployed configuration shown in FIGS. 1A-1C may be about 30 mm or less, such as about 1 mm to about 30 mm, about 1 mm to about 20 mm, about 10 mm to about 20 mm, about 5 mm to about 15 mm, about 8 mm to about 18 mm, about 5 mm to about 10 mm, or greater than 1 mm. In some embodiments, the greatest outer dimension of the ureteral stent 100 (e.g., outer dimension of the resiliently deformable envelope) with the deformable bladder 122 in a delivery configuration (e.g., for deployment) as shown in FIGS. 1D and 1E may be about 10 mm or less, such as about 1 mm to about 5 mm, about 2 mm to about 4 mm, about 1 mm to about 3 mm, about 2.5 mm to about 4.5 mm, about 4 mm to about 6 mm, about 5 mm to about 10 mm, or greater than 2 mm. In some embodiments, the greatest outer dimension of the ureteral stent 100 with the deformable bladder 122 in a delivery configuration may be about 90% less than the greatest outer dimension of the same ureteral stent 100 with the deformable bladder 122 in a deployed configuration, such as about 10% to about 90% less, about 20% to about 80%, about 30% to about 70%, about 10% to about 40%, about 20% to about 50%, or about 5% to about 30% less than greatest outer dimension of the same ureteral stent 100 with the deformable bladder 122 in a deployed configuration. Such delivery configurations may allow the ureteral stent 100 to fit through narrower spaces than when in the deployed configuration, such as during implantation or deployment in a subject.

When deformed, the resiliently deformable envelope 124 may be stretched or compressed along one or more portions of the elongated stent body 110. When in a fully stretched or compressed configuration (e.g., in a delivery sheath), the wall thickness of one or more portions of the resiliently deformable envelope 124 may be reduced by at least about 10% of the deployed configuration wall thickness of the resiliently deformable envelope 124, such as about 10% to about 90%, about 20% to about 80%, about 30% to about 70%, about 40% to about 60%, about 10% to about 30%, about 30% to about 70%, about 70% to about 90%, or about 50% of the deployed configuration wall thickness.

In some embodiments, a length of the resiliently deformable envelope 124 of the deformable bladder 122 in the deployed configuration may be about 10 cm or less, such as about 0.5 cm to about 10 cm, about 1 cm to about 5 cm, about 0.5 cm to about 3 cm, about 1 cm to about 2 cm, about 2 cm to about 3 cm, about 2 cm to about 4 cm, about 3 cm to about 5 cm, about 4 cm to about 8 cm, or greater than about 1 cm. When deformed, the resiliently deformable envelope 124 may extend a length along the elongated stent body 110 (e.g., from a point of attachment thereto). The resiliently deformable envelope 124 in the delivery configuration may exhibit a length (as measured along the longitudinal axis of the stent body) that is 20% longer than the same resiliently deformable envelope 124 in the deployed configuration, such as about 20% to about 200% longer, about 50% to about 150% longer, about 75% to about 125% longer, about 20% longer to about 100% longer, about 300% longer, or about 100% longer than the same resiliently deformable envelope 124 in the deployed configuration.

Returning to FIG. 1A, when positioned in the ureter 150, the lumen 115 of the ureteral stents disclosed herein may provide selectively interrupted fluid communication (e.g., one way flow) between the kidney 152 and the bladder 154. Such a configuration may substantially reduce or prevent urine reflux from the bladder back into the kidney. In an embodiment, the distal end region 120 may be positioned adjacent to or in the bladder 154, such as having a portion thereof extending from the ureteral orifice into the bladder (e.g., deployed on the trigone 155). The proximal end region 130 may be positioned in the kidney 152 of the subject, where the first retaining structure 132 thereof holds the proximal end region 130 in position. The medial segment of the elongated stent body 110 may extend through the ureter between the distal end region 120 and the proximal end region 130. In order to selectively interrupt the fluid communication via the lumen, a ureteral stent may include one or more features therein configured to limit or prevent the flow of fluid from the bladder to the kidney, or vice versa.

Figure 2A:
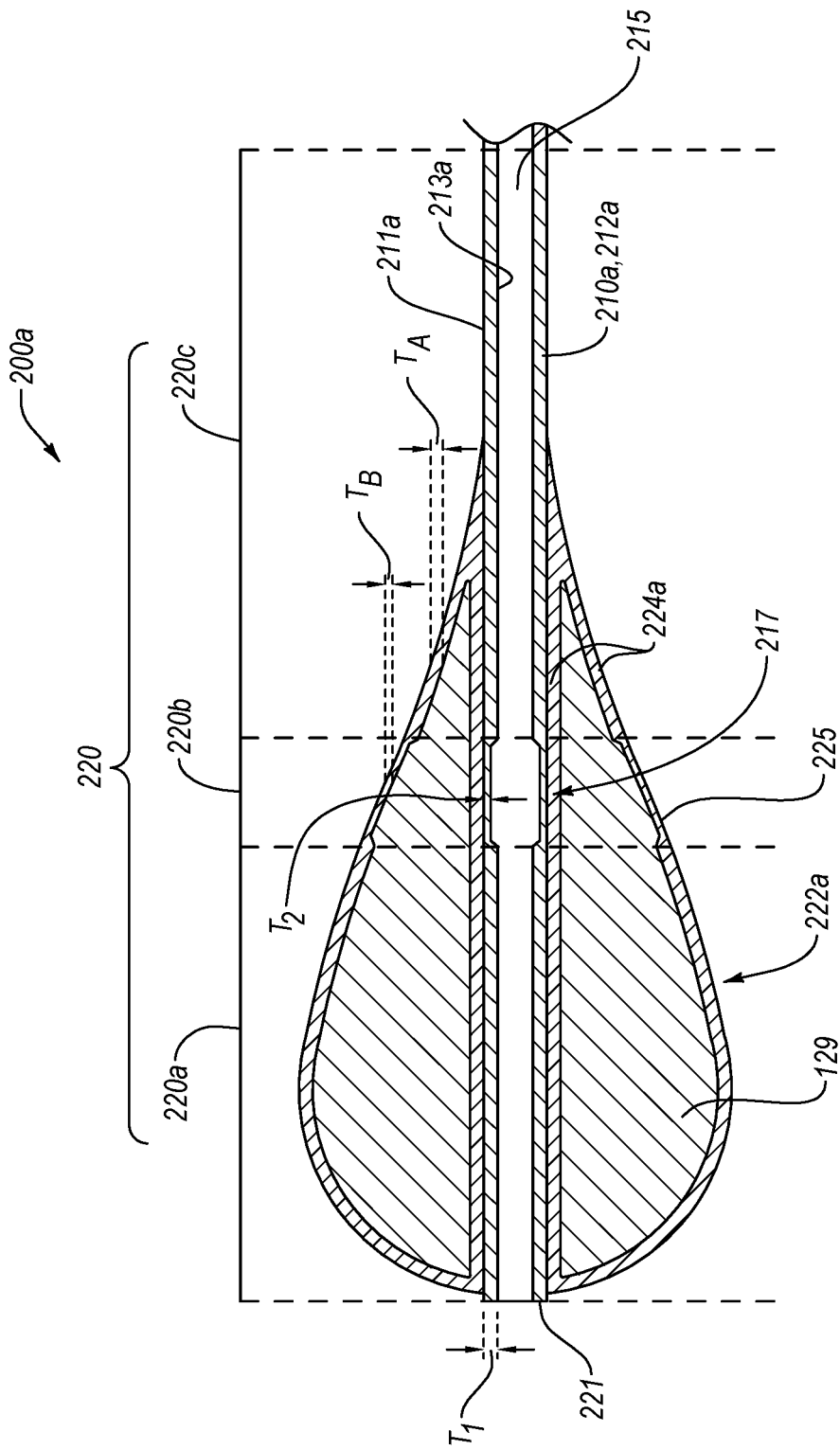

FIG. 2A is a side cross-sectional view of a portion of a ureteral stent 200a according to an embodiment. The ureteral stent 200a may be similar or identical to the ureteral stent 100 in one or more aspects (e.g., size(s), material(s), configuration(s), etc.). For example, the ureteral stent 200a includes the elongated stent body 210a, which may be similar or identical to the elongated stent body 110 in one or more aspects. For example, the elongated stent body 210a includes at least one sidewall 212a having an outer surface 211a and an inner surface 213a, the inner surface defining a lumen 215 that extends completely through the elongated stent body 210a from a distal end 221 of the distal end region 220 to a proximal end (not shown) of the proximal end region (not shown). The ureteral stent 200a includes the deformable bladder 222a, which may be similar or identical to the deformable bladder 122 in one or more aspects. The deformable bladder 222a includes the resiliently deformable envelope 224a and the inert fluid 129, which may be similar or identical to the resiliently deformable envelope 124 in one or more aspects. For example, the resiliently deformable envelope 224a may be substantially toroidal and imperforate (e.g., having no filling ports and/or valves therein) and include the inert fluid 129 sealed therein. The ureteral stent 200a may include one or more portions configured to interrupt the flow of fluid between the distal (first) end region 220 and proximal (second) end region (not shown), such as to prevent urine reflux. For example, the at least one sidewall 212a of the elongated stent body 210a may include one or more portions 217 or regions therein having a thickness different than the remainder of the at least one sidewall 212a. In some embodiments, the resiliently deformable envelope 224a may include one or more portions 225 having a different wall thickness than the rest of the resiliently deformable envelope 224a.

The one or more portions 217 of the elongated stent body 210a may be thinner than the remainder of the at least one sidewall 212a. For example, the at least one sidewall 212a may exhibit a first thickness $T_1$ and the at least one portion 217 may exhibit a second thickness $T_2$, being substantially thinner than the first thickness $T_1$. The first thickness $T_1$ may be selected to provide a flexible yet substantially non-collapsible configuration to the at least one sidewall 212a. The first thickness $T_1$ may be about 50 μm or more, such as about 50 μm to about 250 μm, about 250 μm to about 500 μm, about 500 μm to about 1 mm, about 1 mm to about 3 mm, less than about 3 mm, less than about 2 mm, or about 1 mm. The second thickness $T_2$ may be selected to provide a selectively collapsible second portion 217 (e.g., region) in the at least one sidewall 212a and elongated stent body 210a. In some embodiments, the second thickness $T_2$ may be about 99% of the thickness $T_1$ or less, such as about 10% to about 30%, about 30% to about 60%, about 60% to about 90%, about 50%, about 25%, or about 10% of the thickness $T_1$.

The more proximal segment 220c of the distal end region 220 may be configured to rest in the ureter of a subject. The more medial segment 220b (e.g., portion) of the distal end region 220 may be configured to be positioned in the ureteral orifice in the bladder. The most distal segment 220a of the distal end region 220 may be configured to rest in the bladder of the subject, such as adjacent to or on the trigone of the subject. In some embodiments, the more medial segment 220b of the ureteral stent 200a may include the (second) portion 217 having the second thickness $T_2$. In such embodiments, the at least one sidewall 212a may collapse inward responsive to external pressure (e.g., from the muscles surrounding the bladder during urination) causing the lumen to temporarily occlude. The (second) portion 217 of the at least one sidewall 212a may be constructed of a resilient material (including any of the at least one sidewall materials disclosed herein) configured to return to its original shape when the external pressure subsides. Such an embodiment may allow draining of the kidneys into the bladder while substantially limiting or preventing reflux from the bladder to the kidneys.

In some embodiments, the resiliently deformable envelope 224a may include one or more portions 225 (e.g., regions) having a wall thickness different than the remainder of the resiliently deformable envelope 224a. The one or more portions 225 may be thinner than the remainder of the at least one resiliently deformable envelope 224a. For example, the resiliently deformable envelope 224a may exhibit a first thickness $T_A$ and the at least one portion 225 may exhibit a second thickness $T_B$, being substantially thinner than the first thickness $T_A$. The first thickness $T_B$ may be selected to provide a first stiffness, compliance, or resilience to the resiliently deformable envelope 224a. The first thickness $T_A$ may include any of those thicknesses for a resiliently deformable envelope disclosed herein. The second thickness $T_B$ may be selected to provide a selectively more or less resilient and/or compliant region to the resiliently deformable envelope 224a. In some embodiments, the second thickness $T_B$ may be about 99% of the thickness $T_A$ or less, such as about 10% to about 30%, about 30% to about 60%, about 60% to about 90%, about 50%, about 25%, or about 10% of the first thickness $T_A$.

The more medial segment 220b of the ureteral stent 200a may include the at least one portion 225 having the second thickness $T_B$. In such embodiments, the resiliently deformable envelope 224a may collapse inward responsive to external pressure (e.g., from the muscles surrounding the bladder during urination) allowing the pressure to more easily transfer to the at least one sidewall 212a proximate to the at least one portion 225, which may at least partially cause the lumen to temporarily partially or completely occlude. The resiliently deformable envelope 224a and portions of the at least one sidewall proximate thereto may return to its deployed shape when the external pressure subsides. Such an embodiment may allow draining of the kidneys into the bladder, while substantially limiting or preventing reflux from the bladder to the kidneys.

While shown in the medial segment 220b of the distal end region 220, the second portions 217 and/or 225 having the second thicknesses $T_2$ and $T_B$ may be located in the more proximal segment 220c or the more distal segment 220a of the distal end region 220, such as at the distal end of the elongated stent body 210a. In some embodiments, only one of the at least one sidewall 212a or the resiliently deformable envelope 224a may have a reduced thickness portion. In some embodiments, the second portions 217 and/or 225 having the second thicknesses $T_2$ and $T_B$ may have a longitudinal length of at least about 1 mm, such as about 1 mm to about 2 cm, about 3 mm to about 1.8 cm, about 5 mm to about 1.5 mm, or less than about 2 cm. Such longitudinal lengths may provide a selected amount of variation in positioning of the stent 200a while still allowing compliance prevent reflux.

Figure 2B:
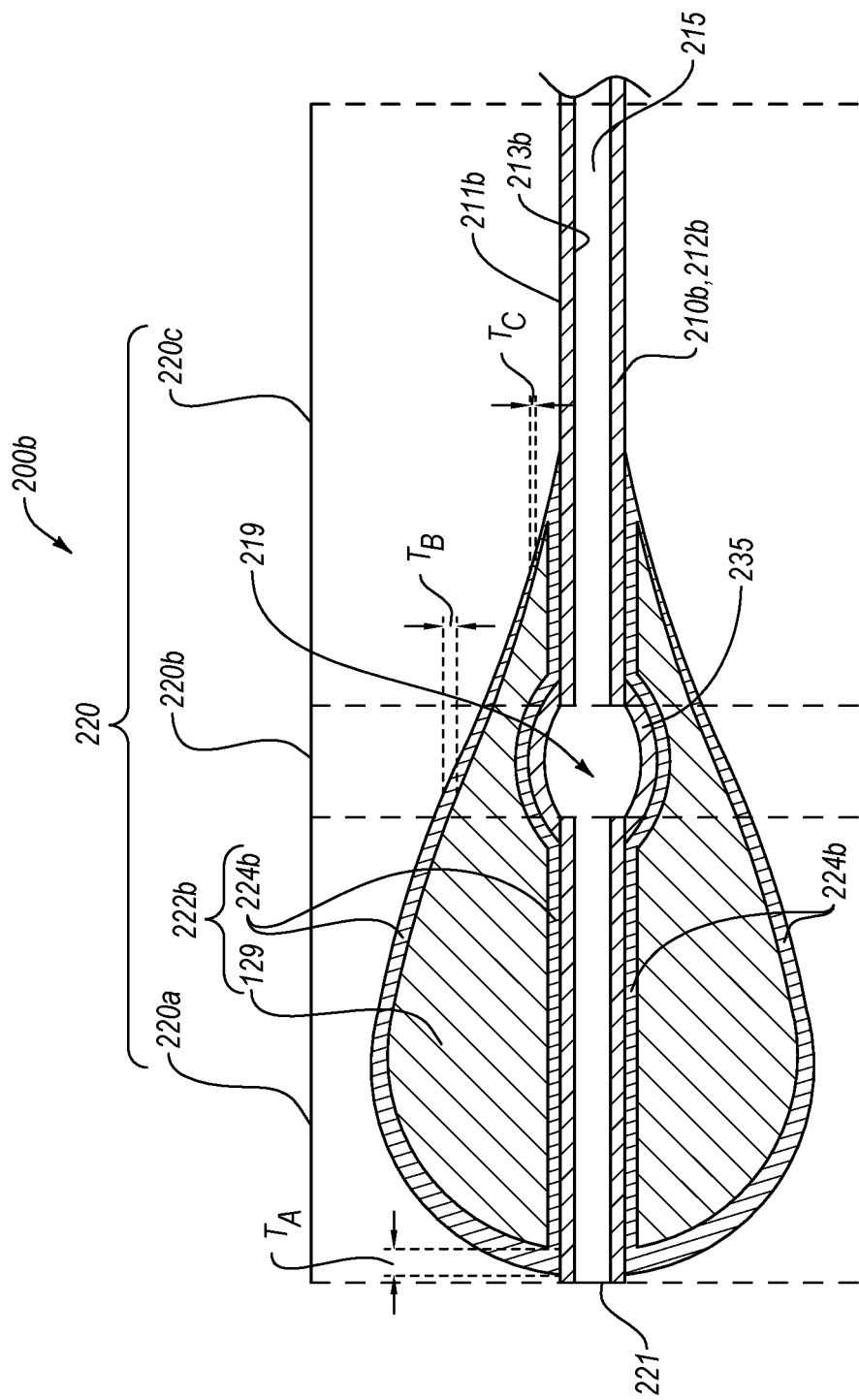

FIG. 2B is a side cross-sectional view of a ureteral stent 200b according to an embodiment. The ureteral stent 200b may be similar or identical to the ureteral stent 100 in one or more aspects (e.g., size(s), material(s), configuration(s), etc.). For example, the ureteral stent 200b includes the elongated stent body 210b, which may be similar or identical to the elongated stent body 110 in one or more aspects. For example, the elongated stent body 210b includes at least one sidewall 212b having an outer surface 211b and an inner surface 213b, with the inner surface 213b defining a lumen 215 that extends completely through the elongated stent body 210b from a distal end 221 of the distal end region 220 to a proximal end (not shown) of the proximal end region (not shown). The ureteral stent 200b includes the deformable bladder 222b, which may be similar or identical to the deformable bladder 122 in one or more aspects. The deformable bladder 222b includes the resiliently deformable envelope 224b and the inert fluid 129, which may be similar or identical to the resiliently deformable envelope 124 in one or more aspects. For example, the resiliently deformable envelope 224b may be substantially toroidal and imperforate (e.g., having no filling ports and/or valves therein) and include the inert fluid 129 sealed therein. The ureteral stent 200b may include one or more portions configured to interrupt the flow of fluid between the distal end region 220 and proximal end region (not shown), such as to prevent urine reflux. For example, the at least one sidewall 212b of the elongated stent body 210b may include one or more discontinuities therein.

The more proximal segment 220c of the distal end region 220 may be configured to rest in the ureter of a subject. The more medial segment 220b of the distal end region 220 may be configured to be positioned in the ureteral orifice in the bladder. The most distal segment 220a of the distal end region 220 may be configured to rest in the bladder of the subject, such as adjacent to or on the trigone of the subject.

The one or more discontinuities may include one or more perforations, gaps, or cut-outs in the at least one sidewall 212b. The one or more discontinuities may allow the at last one sidewall and/or materials (e.g., bridging materials 235) bridging gaps in the at least one sidewall to at least partially (and reversibly) collapse and/or protrude into the lumen 215 to inhibit or prevent fluid flow therethrough. The collapsible portion of the ureteral stent may include one or more of a perforated portion of the at least one sidewall, a discontinuity in the at least one sidewall, a portion of the at least one sidewall having a thinner construction than adjacent portions of the at least one sidewall, or a portion of the at least one sidewall made with a different, a more collapsible material than sidewall material in surrounding portions of the at least one sidewall 212b.

For example, the at least one sidewall 212b may include a gap 219 between a more distal segment 220a and a more proximal segment 220c of the distal end region, such as in the more medial segment 220b of the distal end region 220. The gap 219 may be at least about 2 mm long, such as about 2 mm to about 2 cm, about 5 mm to about 1.5 cm, about 7 mm to about 2 cm, less than about 2 cm, or any other distance suitable to allow the materials therein to comply inward responsive to an external force therein to occlude the lumen. The at least one sidewall may 212b may include one or more bridging materials 235 extending across the gap 219. The one or more bridging materials 235 may be configured to have a greater compliance than the at least one sidewall 212b. The one or more bridging materials 215 are configured to retain the inert fluid 129 therebehind and provide a substantially axially sealed lumen (e.g., allowing only longitudinal flow between the distal and proximal ends). In some embodiments, the one or more bridging materials 235 may be at least a portion of the resiliently deformable envelope 224b, such as an innermost portion of the toroidally shaped resiliently deformable envelope 224b. In some embodiments, the one or more bridging materials 215 may include any of those materials disclosed herein for a resiliently deformable envelope, such as silicone. In an embodiment, the one or more bridging materials 235 may be separate and distinct from the resiliently deformable envelope 224b. For example, the one or more bridging materials 235 may be an additional portion (e.g., layer) of the same material as the resiliently deformable envelope 224b and the one or more bridging materials 235 may displace (e.g., collapse or protrude) into the gap 219 when pressure is applied to the outer surface of the deformable bladder 222b, thereby temporarily occluding the lumen 215 and substantially preventing urine reflux.

In some embodiments, the distal end 221 of the at least one sidewall 212b may extend past the distal extent of the deformable bladder 222b when in a deployed configuration. The portion of at least one sidewall 212b extending past the deformable bladder 222b may cause irritation in a subject (e.g., when the (relatively harder) at least one sidewall contacts the trigone). In other embodiments, the distal end 221 of at least one sidewall 212b may be substantially co-extensive with distal extent of the deformable bladder 222b (FIG. 3A) when in a deployed configuration. In other embodiments, the distal end 221 of at least one sidewall 212b may be recessed in the deformable bladder 222b (FIG. 3B) when in a deployed configuration.

In some embodiments, the resiliently deformable envelope 224b may include one or more portions 225 having a different wall thickness than the rest of the resiliently deformable envelope 224b, such as tapering from a thicker wall at the more distal segment 220a to a thinner wall at the more proximal segment 220c. Such embodiments may allow the resiliently deformable envelope 224b to displace axially along the elongated stent body 210b responsive to less external pressure than embodiments having a uniform wall thickness of the resiliently deformable envelope. For example, the at least resiliently deformable envelope 224b may exhibit a first thickness $T_A$ tapering to a second thickness $T_B$ being substantially thinner than the first thickness $T_A$, and tapering to a third thickness $T_C$, the third thickness $T_C$ being thinner than the second thickness $T_B$. The first thickness $T_A$, second thickness $T_B$, and/or third thickness $T_C$, may be selected to provide a selected profile of elasticity, compliance, or resilience to the resiliently deformable envelope 224b. The first thickness $T_A$ may include any of those thicknesses for a resiliently deformable envelope disclosed herein. The second thickness $T_B$ and/or the third thickness $T_C$ may be selected to provide a selectively more or less resilient and/or compliant region to the resiliently deformable envelope 224a. In some embodiments, the second thickness $T_B$ may be about 90% of the thickness $T_A$ or less, such as about 10% to about 30%, about 30% to about 60%, about 60% to about 90%, about 50%, about 25%, or about 10% of the thickness $T_A$. In some embodiments, the third thickness $T_C$ may be about 90% of the second thickness $T_B$ or less, such as about 10% to about 30%, about 30% to about 60%, about 60% to about 90%, about 50%, about 25%, or about 10% of the second thickness $T_B$.

While depicted with both, in some embodiments, a ureteral stent may include only the one or more discontinuities in the at least one sidewall 212b or tapered resiliently deformable envelope 224b. While shown tapering from a thicker wall at the distal segment to a thinner wall at the more proximal portion of the resiliently deformable envelope 224b, some embodiments may taper from a thicker wall outward from the medial segment to thinner wall(s) at the more proximal and/or distal segments of the resiliently deformable envelope.

In some embodiments, the resiliently deformable envelope may taper from a thicker wall at the more proximal segment to a thinner wall at the more distal segment. FIGS. 2C and 2CC are side cross-sectional views of an embodiment of a ureteral stent 200c in deployed and delivery configurations, respectively. The ureteral stent 200c is similar or identical to the ureteral stent 200b in one or more aspects. For example, the elongated stent body 210c includes at least one sidewall 212c having an outer surface 211c and an inner surface 213c, the inner surface 213c defining a lumen 215 that extends completely through the elongated stent body 210c from a distal end 221 of the distal end region 220 to a proximal end (not shown) of the proximal end region (not shown). The ureteral stent 200b may be similar or identical to the ureteral stent 200c, except that the ureteral stent 200c may include, and is depicted with, a uniform at least one sidewall 212c (and elongated stent body 210c) and the resiliently deformable envelope 224c tapers from a thinner first wall thickness $T_A$ at the more distal segment 220a of the distal end region 220; to a second wall thickness $T_B$ being thicker than the first wall thickness $T_A$; to a third wall thickness $T_C$ being thicker than the second wall thickness $T_B$. In such embodiments, the steadily or generally continuously increasing wall thickness of the resiliently deformable envelope 224c, as a function of distance from the distal end of the ureteral stent 200c, may provide a more resiliently deformable bladder 222c and increased compliance and comfort in the subject (e.g., thinner resiliently deformable envelope walls being softer and more compliant on the trigone). The resiliently deformable envelope 224c may be substantially toroidal and imperforate (e.g., having no filling ports and/or valves therein) and include the inert fluid 129 sealed therein. In some embodiments, both the innermost and outermost portions of the walls of the resiliently deformable envelope 224c may be tapered as described above. In some embodiments, only one of the innermost and outermost portions of the resiliently deformable envelope 224c may be tapered as described above, with the remaining portion(s) having a substantially uniform wall thickness.

In some embodiments, the second thickness $T_B$ may be about 10% larger than the thickness $T_A$ or more, such as about 10% to about 30%, about 30% to about 60%, about 60% to about 90%, about 50%, about 25%, or about 10% larger than the thickness $T_A$. In some embodiments, the third thickness $T_C$ may be about 10% larger than the second thickness $T_B$ or more, such as about 10% to about 30%, about 30% to about 60%, about 60% to about 90%, about 50%, about 25%, or about 10% larger than the second thickness $T_B$.

The thicker portion of the resiliently deformable envelope 224c may provide a more resilient structure. Put another way, the thicker material adjacent to the more proximal segment of the ureteral stent may provide a greater returning force on the inert fluid 129, such that the deformable bladder 222c returns to a deployed shape faster or under more pressure than a resiliently deformable envelope having a uniform wall thickness or opposite taper.

As shown in FIG. 2CC, in response to external pressure P (such as applied by a delivery sheath), the inert fluid 129 may be forced toward the more proximal segment 220c of the resiliently deformable envelope 224c, thereby reducing the radial cross-sectional dimension of the resiliently deformable envelope 224c, deformable bladder 222c, and ureteral stent 200c. Upon removal of the pressure P, such as upon removal from a delivery sheath, the deformable bladder 222c may return to the deployed shape shown in FIG. 2C. The thicker wall at the more proximal segment 220c may allow a faster return to a deployed shape.

Figure 2D:
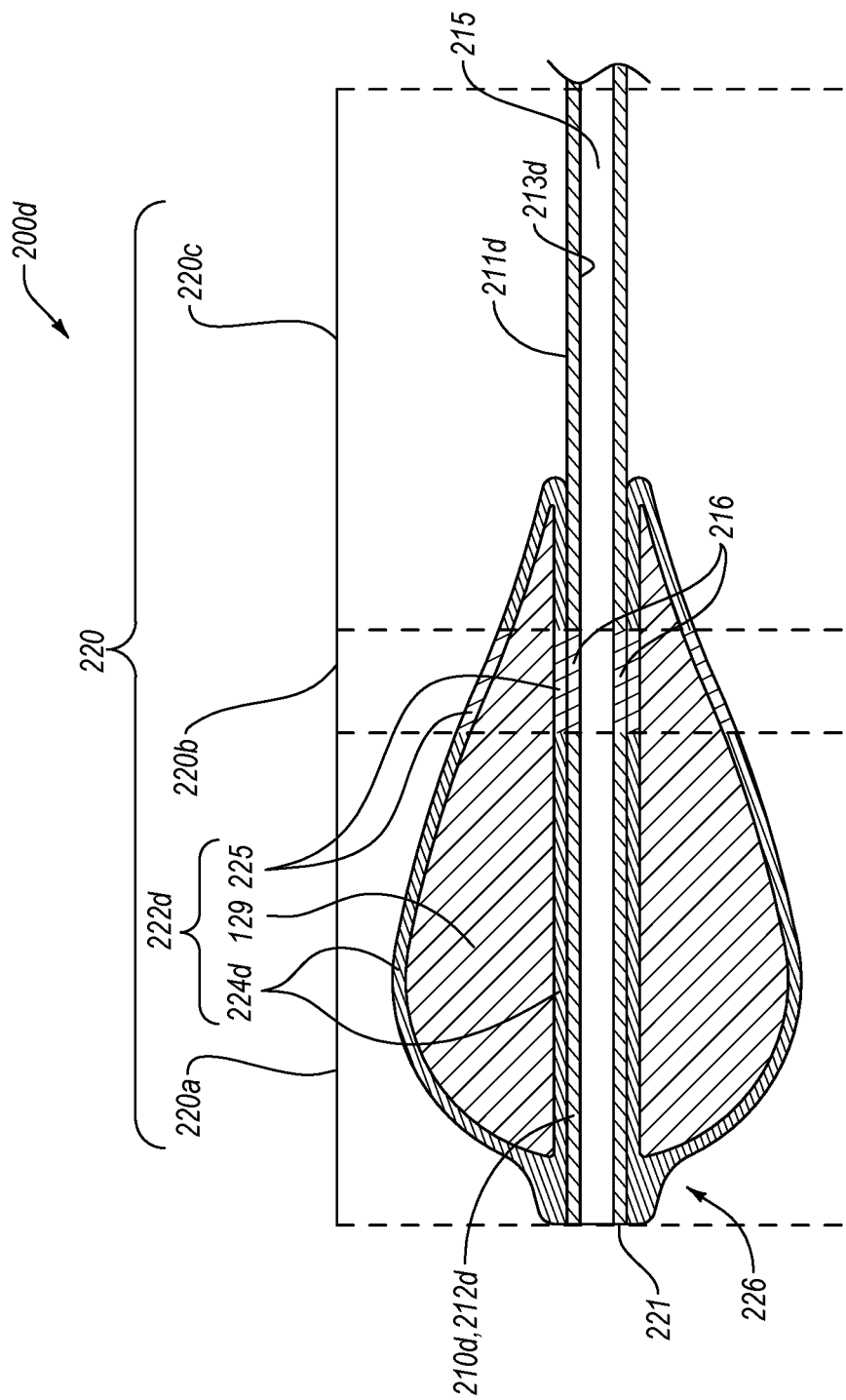

FIG. 2D is a side cross-sectional view of a portion of a ureteral stent 200d according to an embodiment. The ureteral stent 200d may be similar or identical to the ureteral stent 100 in one or more aspects (e.g., size(s), material(s), configuration(s), etc.). For example, the ureteral stent 200d includes the elongated stent body 210d, which may be similar or identical to the elongated stent body 110 in one or more aspects. For example, the elongated stent body 210d includes at least one sidewall 212d having an outer surface 211d and an inner surface 213d, the inner surface defining a lumen 215 that extends completely through the elongated stent body 210d from a distal end 221 of the distal end region 220 to a proximal end (not shown) of the proximal end region (not shown). The ureteral stent 200d includes the deformable bladder 222d, which may be similar or identical to the deformable bladder 122 in one or more aspects. For example, the resiliently deformable envelope 224d may be substantially toroidal and imperforate (e.g., having no filling ports and/or valves therein) and include the inert fluid 129 sealed therein. The deformable bladder 222d includes the resiliently deformable envelope 224d and the inert fluid 129, which may be similar or identical to the resiliently deformable envelope 124 in one or more aspects. For example, the resiliently deformable envelope 224d may be made of silicone and the inert fluid may be mineral oil. The ureteral stent 200d may include one or more portions configured to interrupt the flow of fluid between the distal end region 220 and proximal end region (not shown), such as to prevent urine reflux. For example, the at least one sidewall 212d of the elongated stent body 210d may include one or more portions 216 (e.g., regions) therein having a different material than the remainder of the at least one sidewall 212d. In some embodiments, the resiliently deformable envelope 224d may include one or more portions 225 (e.g., regions) having a different material in the resiliently deformable envelope wall than the rest of the resiliently deformable envelope 224d.

The one or more portions 216 may be made with a different material than the remainder of the at least one sidewall 212d. For example, the at least one sidewall 212d may exhibit a first material (e.g., first sidewall material) in the more distal and/or proximal segments 220a and 220c and the at least one portion 216 may include at least a second material (e.g., second sidewall material) different than the first material in the medial segment 220b. The first material may be selected to provide a flexible yet substantially non-collapsible configuration to the at least one sidewall 212d. The first material may include any of those materials for a sidewall disclosed herein. The second material may be selected to provide a selectively collapsible portion 216 in the at least one sidewall 212d and elongated stent body 210d. For example, the second material may exhibit a lower modulus of elasticity, and therefore exhibit higher compliance responsive to forces thereon than the first, relatively stiffer material. The first material may be nitinol and the second material may include a silicone-containing polyurethane having a lower modulus of elasticity. In some embodiments, the second material may exhibit a modulus of elasticity greater than the first material.

The more proximal segment 220c of the distal end region 220 may be configured to rest in the ureter of a subject. The more medial segment 220b of the distal end region 220 may be configured to be positioned in the ureteral orifice in the bladder. The most distal segment 220a of the distal end region 220 may be configured to rest in the bladder of the subject, such as adjacent to or on the trigone of the subject. In some embodiments, the more medial segment 220b of the ureteral stent 200a may include the at least one portion 216 having the second material therein. In such embodiments, the at least one portion 216 of the at least one sidewall 212d may collapse inward response to external pressure (e.g., from the muscles surrounding the bladder during urination) thereby causing the lumen to temporarily occlude. The at least one portion 216 of the at least one sidewall 212d may be constructed of a resilient material (including any of the at least one sidewall materials disclosed herein) configured to return to its original shape when the external pressure subsides. Such an embodiment may allow draining of the kidneys into the bladder while substantially limiting or preventing reflux from the bladder to the kidneys.

In some embodiments, the resiliently deformable envelope 224d may include one or more portions 225 (e.g., regions) having a material different than the remainder of the resiliently deformable envelope 224d. The one or more portions 225 may be more or less compliant and/or resilient than the remainder of the resiliently deformable envelope 224d. For example, the resiliently deformable envelope 224d may include a first material (e.g., first resiliently deformable envelope material) in the more distal and proximal segments 220a and 220c and a second material (e.g., second resiliently deformable envelope material) in the portion 225 in the more medial segment 220b of the distal end region 220. The first material may be selected to provide a first modulus of elasticity, compliance, or resilience to the resiliently deformable envelope 224d. The first material may include any of those materials for a resiliently deformable envelope disclosed herein. The second material may be selected to provide a selectively more or less resilient and/or compliant region to the resiliently deformable envelope 224d. In some embodiments, the second material may be selected to have a lower or higher compliance and/or resilience than the first material. The second material may include any of those materials disclosed for a resiliently deformable envelope herein, wherein the second material has a lower or greater amount of resilience and/or compliance than the first material. For example, the first material may include a first silicone and the second material may include a second silicone (or a natural rubber) having a lower modulus of elasticity than the first material.

In such embodiments, the one or more portions 225 of the resiliently deformable envelope 224d may collapse inward responsive to external pressure (e.g., from the muscles surrounding the bladder during urination), thereby allowing more pressure to transfer to the at least one sidewall 212d and/or at least one portion 216 therein. Such an embodiment may allow the lumen to temporarily occlude more easily than an embodiment having a uniform resiliently deformable envelope material therethrough. While shown with both a first and second material in the resiliently deformable envelope 224d and at least one sidewall 212d, in some embodiments, only one of the at least one sidewall 212d or resiliently deformable envelope 224d may include more than one material therein. For example, in some embodiments, only the at least one sidewall 212d may include a portion having a first material and at least a second portion having a second, different material.

As shown in FIG. 2D, in some embodiments, the distal most portion of the resiliently deformable envelope 224d may include a nipple 226 extending about the distal most portion of the at least one sidewall 212d. The nipple may include a length of resiliently deformable envelope 224d material, having a minimal (lateral) cross-section, secured or anchored to the outer surface of the at least one sidewall 212d. The nipple 226 may be about 1 mm long or greater, such as about 1 mm to about 2 cm, about 2 mm to about 5 mm, about 5 mm to about 1 cm, or about 1 cm to about 2 cm, or less than about 2 cm. In some embodiments, the nipple 226 may taper from a smallest diameter at the distal most end of the ureteral stent 200d to a greater diameter as a function of the distance away from the distal most portion of the ureteral stent 200d. Any of the embodiments herein may include a nipple 226.

Figure 3A:
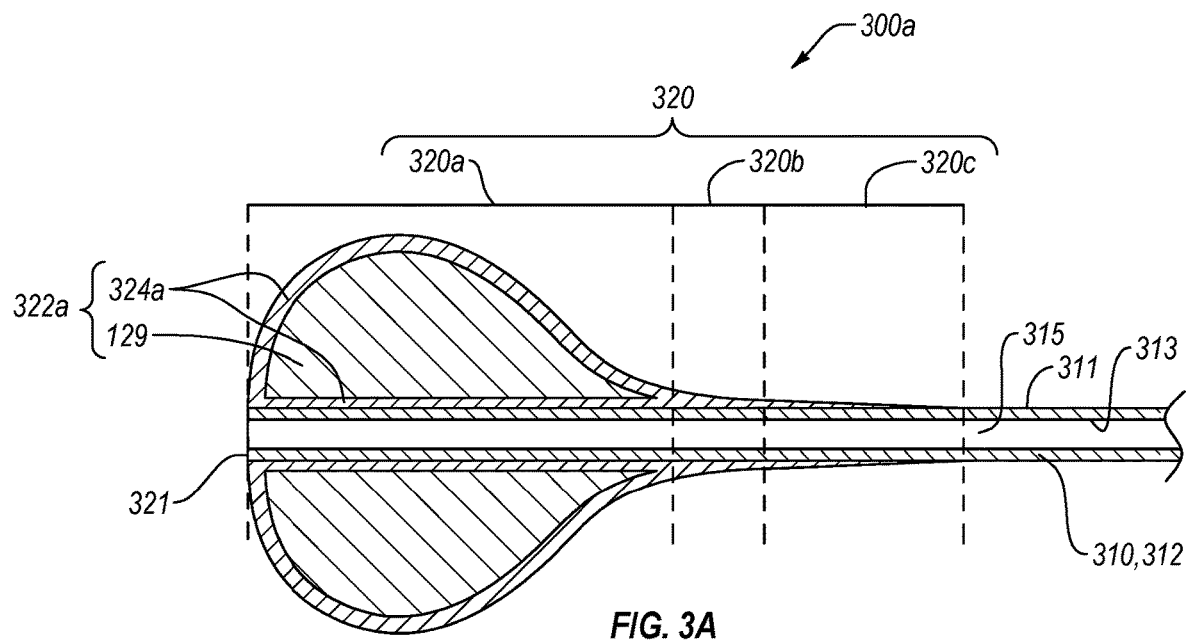
FIGS. 3A and 3B are side cross-sectional views of portions of ureteral stents according to embodiments.
Figure 3B:
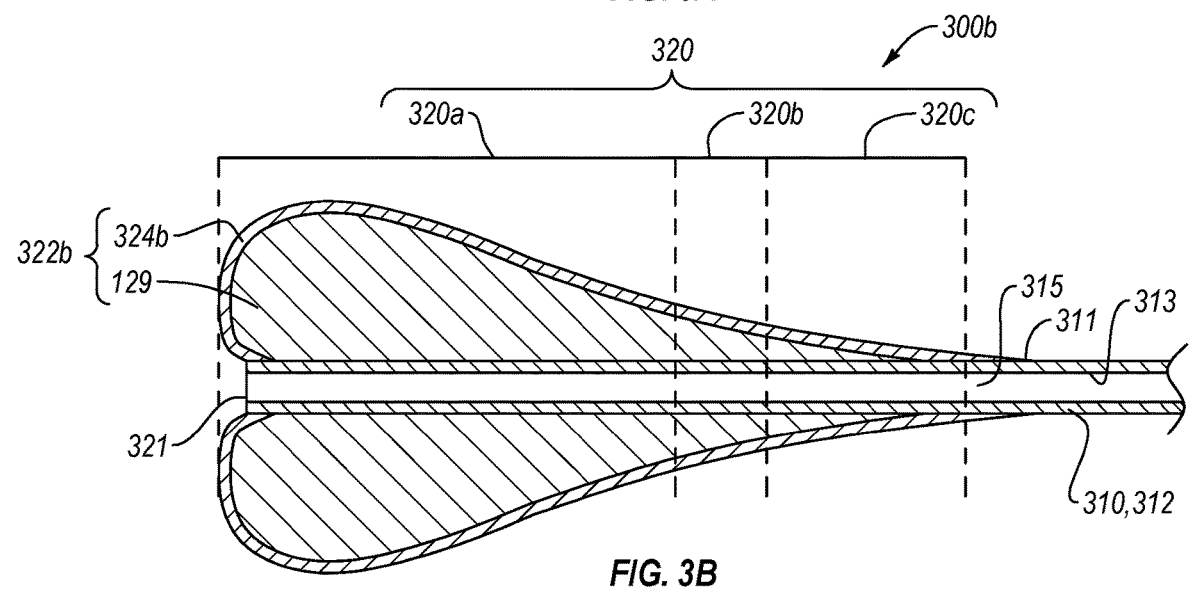

The deformable bladders herein may have any of a variety of different (longitudinal) cross-sectional shapes. FIGS. 3A and 3B depict side cross-sectional views of longitudinal shapes of two different ureteral stents according to different embodiments. FIG. 3A depicts the cross-sectional shape of ureteral stent 300a according to an embodiment. The ureteral stent 300a may include an elongated stent body 310 includes at least one sidewall 312 defining a lumen 315 therethrough. The at least one sidewall 312 includes an outer surface 311 and an inner surface 313, the inner surface defining the lumen 315 that extends completely through the elongated stent body 310 from a distal end 321 of the distal end region 320 to a proximal end (not shown) of the proximal end region (not shown). The elongated stent body 310 includes a deformable bladder 322a secured thereto and at least partially (circumferentially) surrounding the at least one sidewall 312 at the distal end region 320. The deformable bladder 322a includes a resiliently deformable envelope 324a and an inert fluid 129 therein. The elongated stent body 310, at least one sidewall 312, and deformable bladder 322a may be similar or identical to any elongated stent body, at least one sidewall, or deformable bladder disclosed herein, including but not limited to material composition, dimension(s), and location(s). The deformable bladder 322a includes a resiliently deformable envelope 324a having a substantially teardrop deployed shape. The teardrop deployed shape may include the bulbous portion of the bottom of the teardrop in the more distal segment 320a of the distal end region 320, which narrows somewhat in the more medial segment 320b, to a narrowest portion capable of fitting into a ureter at the proximal segment 320c of the distal end region 320.

The bulbous portion of the teardrop in the more distal segment 320a may be configured to rest in the bladder (or kidney) of a subject, thereby providing a soft, compliant interface with the bladder, such as on the trigone. The large surface area of the bulbous portion of the deformable bladder 322a may serve to spread the pressure between the portions of the subject (e.g., bladder) in contact with the ureteral stent over a relatively large area, thereby reducing or eliminating irritation and discomfort experienced with smaller point of contact such as from the elongated stent body. The more medial segment 320b of the resiliently deformable envelope 324a may be sized and configured to provide a tight fit with the ureteral orifice of the subject. Such a configuration may limit or prevent reflux of urine from the bladder to kidneys. As shown, in some embodiments, the end of the at least one sidewall 312 may be substantially flush with the most distal segment of the deformable bladder 322a when in a deployed configuration.

FIG. 3B depicts the cross-sectional shape of ureteral stent 300b according to an embodiment. The ureteral stent 300b may similar to the ureteral stent 300a in one or more aspects. The elongated stent body 310 includes the deformable bladder 322a at least partially surrounding the at least one sidewall 312 at the distal end region 320. The deformable bladder 322b includes the resiliently deformable envelope 324b and an inert fluid 129 therein.

As shown, in some embodiments, the resiliently deformable envelope 324b may not be toroidal. For example, a single layer of the resiliently deformable envelope 324b may be secured to the elongated stent body 310. The resiliently deformable envelope 324b may be secured to the elongated stent body 310 at a distal most segment 320a of the distal end region 320 and the proximal segment 320c of the distal end region 320 of the elongated stent body. The resiliently deformable envelope 324b may be secured to the at least one sidewall 312 with one or more of an adhesive (e.g., an epoxy), integral formation (e.g., fit in or on one or more flanges on the elongated stent body 310), interference fit, one or more retainers (e.g., clamps, clips, etc.), or any other suitable technique of securing the resiliently deformable envelope to an elongated stent body. In such embodiments, the cavity in which the inert fluid 129 is disposed may be defined by and between the outer surface 311 of the at least one sidewall 312 and an inner surface of the resiliently deformable envelope 324b. In an embodiment, the inert fluid 129, such as mineral oil, may be imperforately sealed between the elongated stent body 310 and the resiliently deformable envelope 324b, such as a silicon envelope, prior to deployment (e.g., prior to insertion into a subject). In such embodiments, neither the resiliently deformable envelope 324b nor the elongated stent body 310 have a fill port or other filling means therein. Rather, the inert fluid is sealed in the deformable bladder prior to delivery into the subject, such as at a manufacturer. The prefilled deformable bladders 322b may be ready for delivery and deployment into a subject without adding more inert fluid prior to use.

The deformable bladder 322b exhibits a more exaggerated or elongated teardrop shape than the deformable bladder 322a described above, with a relatively longer and flatter bulbous portion at the more distal segment 320a than the deformable bladder 322a. The bulbous portion of the bottom of the teardrop in the more distal segment 320a of the distal end region 320 may exhibit a substantially flatter distal end than the substantially more spherical bulbous portion of the deformable bladder 322a. Additionally, the medial segment of the deformable bladder 322b may be substantially wider than the medial segment of the deformable bladder 322a.

The deformable bladder 322b may taper over a longer longitudinal distance than the deformable bladder 322a. The taper may begin in the more distal segment 320a, extending through the more medial segment 320b, and into the more proximal segment 320c.

The bulbous portion of the teardrop in the more distal segment 320a may be configured to rest in the bladder (or kidney) of a subject, thereby providing a soft, compliant interface with the bladder, such as on the trigone. The large surface area of the bulbous portion of the deformable bladder 322a may serve to spread the pressure between the portions of the subject (e.g., bladder) in contact with the ureteral stent over a relatively large area, thereby reducing or eliminating irritation and discomfort experienced with smaller point of contact such as from the elongated stent body. The more medial segment 320b of the deformable bladder 322b may be sized and configured to provide a tight fit with the ureteral orifice of the subject. Such a configuration may limit or prevent reflux of urine from the bladder to kidneys. As shown, in some embodiments, the end of the at least one sidewall 312 may be recessed into the most distal segment of the deformable bladder 322a when in a deployed configuration. The end of the at least one sidewall 312 may be recessed into the deformable bladder 322 by 500 µm or more, such as about 500 µm to about 3 mm, or about 1 mm to about 2 mm.

In some embodiments, the more distal segment 320a may extend inwardly at least about 1 mm from the distal end of the at least one side wall 312, such as about 1 mm to about 2 cm, or about 2 mm to about 1 cm, or less than about 2 cm from the distal end of the at least one side wall 312, in a deployed configuration. In some embodiments, the more medial segment 320b may extend inwardly at least about 1 mm from the more distal segment 320a, such as about 1 mm to about 2 cm, or about 2 mm to about 1 cm, or less than about 2 cm from the more distal segment 320a, in a deployed configuration. In some embodiments, the more proximal segment 320c may extend inwardly at least about 1 mm from the more medial 320b, such as about 1 mm to about 2 cm, or about 2 mm to about 1 cm, or less than about 2 cm from the more medial segment 320b, in a deployed configuration. In some embodiments, the more distal segment 320a may be longer than the more medial segment 320b, in a deployed configuration. In some embodiments, the more proximal segment 320c may be longer than the more medial segment 320b, in a deployed configuration. In embodiments, the more medial segment 320b may be longer than one or more of the more distal segment 320a or the more proximal segment 320c, in a deployed configuration.

Further longitudinal cross-sectional shapes are also contemplated by the present disclosure according to various other embodiments, such as a generally pear-shaped, generally kidney-shaped, generally spherical, generally cylindrical, other shaped deformable bladder (when in a deployed configuration), or combinations of any of the foregoing.

The deformable bladder of the ureteral stents herein may include any of a variety of lateral/radial cross-sectional shapes (e.g., looking down the longitudinal axis of the elongated stent body). FIGS. 3C-3F, depict transverse cross-sectional views of different embodiments of ureteral stents having different shapes, when in a deployed configuration.

Figure 3C:
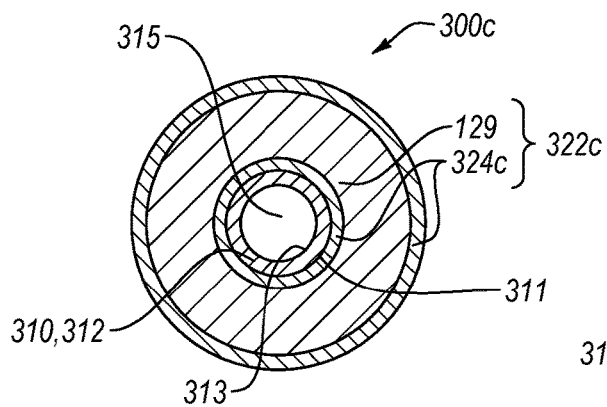
FIGS. 3C-3F are transverse cross-sectional views of portions of ureteral stents according to embodiments.

As shown in FIG. 3C, the transverse cross-sectional shape may be substantially circular (e.g., round). The ureteral stent 300c includes the substantially circular shaped deformable bladder 322c, which includes the substantially circular shaped resiliently deformable envelope 324c and the inert fluid 129. The inert fluid 129 may be contained within the resiliently deformable envelope 324c. In some embodiments, the outer and/or inner walls 311 and 313 of the elongated stent body 310 may be concentric with the substantially circular (radially extending shape) resiliently deformable envelope 324c.

Figure 3D:
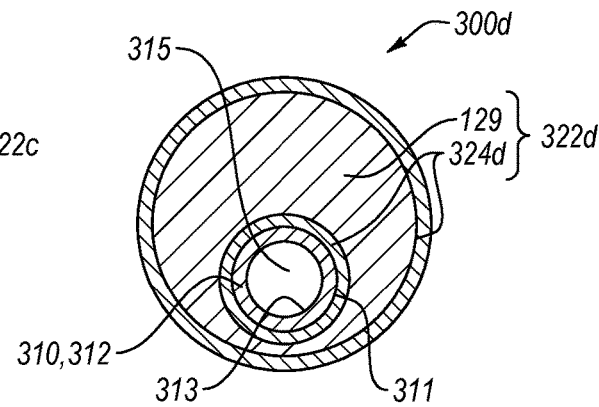

As shown in FIG. 3D, in some embodiments, the elongated stent body may be non-concentric with the deformable bladder. For example, the ureteral stent 300d includes the substantially circular (radially extending shape) deformable bladder 322d, which includes the substantially circular resiliently deformable envelope 324d and the inert fluid 129. The inert fluid 129 being contained within the resiliently deformable envelope 324d. The elongated stent body 310 may be offset from a concentric configuration with the resiliently deformable envelope 324d such that the outer and/or inner surfaces 311 and 313 of elongated stent body 310 are closer to one or more portions of the resiliently deformable envelope 324d than the remainder thereof.

Figure 3E:
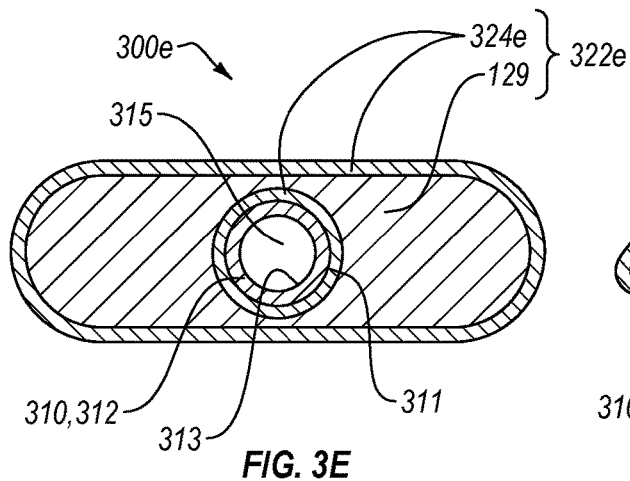

As shown in FIG. 3E, the transverse cross-sectional shape may be substantially oval shaped, such as the substantially oblong oval shape depicted. Any oval shape may be used. Additionally, other shapes having a substantially oblong configuration may be used (e.g., an oblong rectangle, etc.). Such embodiments may allow the deformable bladder 322e to have a smaller cross-sectional shape in a single dimension, and be capable of lying flat in the subject. The ureteral stent 300e includes the oblong oval (radially extending) shaped deformable bladder 322e, which includes the oblong oval shaped resiliently deformable envelope 324e and the inert fluid 129. The inert fluid 129 being contained within the resiliently deformable envelope 324e.

Figure 3F:
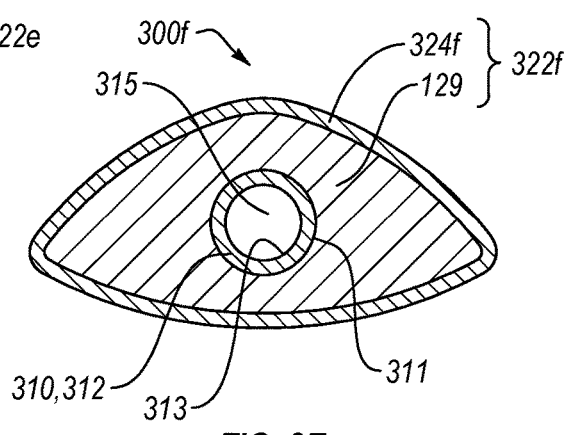

As shown in FIG. 3F, a deformable bladder 322f may exhibit a lens-like (e.g., biconvex) transverse cross-sectional shape. In some embodiments, the lens shape may be substantially symmetrical with respect to each convex portion thereof. In some embodiments, the lens shape may be substantially non-symmetrical with respect to each convex portion thereof (e.g., each side having a different radius or radii than the remaining side). In some embodiments, the lens shape may include one or more rounded ends between the biconvex portions to reduce discomfort in the subject due to relatively sharp angles in the stent. The ureteral stent 300f includes the non-symmetrical lens shaped deformable bladder 322f, which includes the non-symmetrical lens shaped resiliently deformable envelope 324f and the inert fluid 129. In some embodiments (FIG. 3B), the inert fluid 129 may be contained (e.g., imperforately sealed) between the resiliently deformable envelope 324f and the at least one sidewall 312 of the elongated stent body 310 (e.g., the cavity in which the inert fluid 129 is contained is formed by the elongated stent body 310 and the resiliently deformable envelope 324f secured thereto) as shown in FIG. 3F. For example, a silicone resiliently deformable envelope 324f and outer surface 311 of the elongated stent body 312 may form a cavity in which mineral oil inert fluid 129 is sealed.

As noted above, FIGS. 3C-3F depict deployed (e.g., un-deformed and/or expanded) cross-sectional shapes. During use, the relatively compliant resiliently deformable envelopes may radially distort (e.g., changing the radial cross-sectional shape thereof) to comply with force(s) applied thereto. Accordingly, the shapes considered herein may be at least partially distorted to comply with internal pressure from the subject during use.

In some embodiments (not shown), the deployed cross-sectional shape of a resiliently deformable envelope may include one or more deployed cross-sectional shapes. For example, a ureteral stent may include a substantially round cross-sectional shape in the region configured to be positioned at the ureteral orifice in the bladder, and transition along the longitudinal length of the ureteral stent to a substantially oblong oval at a distal end thereof configured to rest on or near the trigone of the subject.

While shown as substantially round in cross-section (e.g., cylindrical), in some embodiments, at least a portion of the elongated stent bodies disclosed herein may be substantially non-circular, such as having a cross-sectional shape of an oval, a flat oval, polygonal, tear-drop, semi-circular, tri-lobal, distortions or variations of any of the foregoing, an amorphous shape, or combinations of any of the foregoing.

In any of the above embodiments, the resiliently deformable envelope may be substantially toroidal (without regard to longitudinal shape), having a substantially continuous wall. The substantially continuous wall may include an inner portion (e.g., radially inward facing portion of the doughnut hole in the toroid) adjacent to the outer surface of the at least one sidewall and an outer (e.g., radially outward facing) portion distal to the at least one sidewall. The inert fluid 129 may be retained inside of the toroidal resiliently deformable envelope (e.g., without contacting the at least one sidewall). In such embodiments, at least a portion of the inner portion of the resiliently deformable envelope may be secured to the outer surface of the at least one sidewall at one or more locations therealong. The resiliently deformable envelope may be secured to the at least one sidewall with one or more of an adhesive (e.g., an epoxy), integral formation (e.g., fit in or on one or more flanges on the elongated stent body 110), interference fit, one or more retainers (e.g., clamps, clips, etc.), or any other means of securing a resiliently deformable envelope to an elongated stent body.

In some embodiments, a ureteral stent may include more than one deformable bladder. In such embodiments, the first retaining structure (FIG. 1B) may be a deformable bladder, such as any deformable bladder disclosed herein. FIGS. 4A and 4B are cross sectional views of ureteral stents having a deformable bladder at both the distal and proximal end regions thereof.

FIG. 4A is a cross-sectional view of an embodiment of a ureteral stent 400a having a first deformable bladder 422 at a distal end region 420 and a second deformable bladder 422a at a proximal end region 430 of a sidewall 412 of an elongated stent body 410. The at least one sidewall 412 and the elongated stent body 410 may be similar or identical to any sidewall and the elongated stent body disclosed herein, including any individual aspects thereof. For example, the elongated stent body 410 includes at least one sidewall 412 having an outer surface 411 and an inner surface 413, the inner surface defining a lumen 415 that extends completely through the elongated stent body 410 from a distal end 421 of the distal end region 420 to a proximal end 431 of the proximal end region 430. The first deformable bladder 422 includes a resiliently deformable envelope 424 and an inert fluid 129 similar or identical to any resiliently deformable envelope or inert fluid disclosed herein, including any individual aspects thereof. The ureteral stent 400a includes a second deformable bladder 422a at the proximal end region 430. The second deformable bladder 422a being configured to comfortably rest in the ureteral orifice in the kidney of a subject. For example, the second deformable bladder 422a may be configured similarly or identically to the first deformable bladder 422. The second deformable bladder 422a includes the resiliently deformable envelope 424a having the inert fluid 129a therein. When deployed in a subject, the first deformable bladder 422 on the distal end region 420 may be positioned adjacent to the trigone of in the bladder of a subject and the second deformable bladder 422a may be positioned in the kidney of the subject, each providing a comfortable, compliant retainer in the respective anatomical structures of the subject with a lumen fluidly connecting the kidney and bladder. In some embodiments, each of the first and second deformable bladders 422 and 422a may be substantially identical.

In some embodiments, the first deformable bladder 422 and second deformable bladder may be substantially different in one or more aspects. FIG. 4B is a cross-sectional view of a ureteral stent 400b having a first deformable bladder 422 and a second deformable bladder 422b differing in at least one aspect. The ureteral stent 400b may be similar or identical to the ureteral stent 400a in one or more aspects. For example the ureteral stent 400b includes the elongated stent body 410 having at least one sidewall 412, outer surface 411, inner surface 413, lumen 415 terminating at the distal end 421 of the distal end region 420 and proximal end 431 of the proximal end region 430. The ureteral stent 400b includes the first deformable bladder 422 at the distal end region 420, as disclosed above. The ureteral stent 400b includes a second deformable bladder 422b including the resiliently deformable envelope 424b and inert fluid 129b at the proximal end region 430. One or more portions of the second deformable bladder 422b may have a different configuration than the first deformable bladder 422. For example, the second deformable bladder 422b may include a substantially different shape than the first deformable bladder 422, such as to substantially complement the different anatomical environments in the intended deployment location(s) (e.g., bladder and kidney) of a subject. In an embodiment, the first deformable bladder 422 may include any shape for a deformable bladder and/or resiliently deformable envelope disclosed herein and the second deformable bladder 422b may include any shape disclosed shape for a deformable bladder and/or resiliently deformable envelope herein different from the first deformable bladder 422. As shown, the first deformable bladder 422 may be tear-drop shaped and the second deformable bladder 422b may be substantially spheroid (e.g., a more spherical shape than the first deformable bladder 422), which may be toroidal. In some embodiments, the first and second deformable bladders 422 and 422b may have one or more of different shapes, size(s), material(s) (e.g., thicknesses of resiliently deformable envelope, types of resiliently deformable envelope material, inert fluid(s)), pressures in the deformable bladder (e.g., comparatively more or less inert fluid in an resiliently deformable envelope), amount of at least one side wall protruding therefrom or therein, or any other characteristic. For example, the resiliently deformable envelope 424 of the first deformable bladder 422 may have a different wall thickness and/or material then the resiliently deformable envelope 424b of the second deformable bladder 422b. In an embodiment, the inert fluid 129 in the first deformable bladder may be different or in a greater quantity than the inert fluid 129b in the second deformable bladder 422b.

Figure 5:
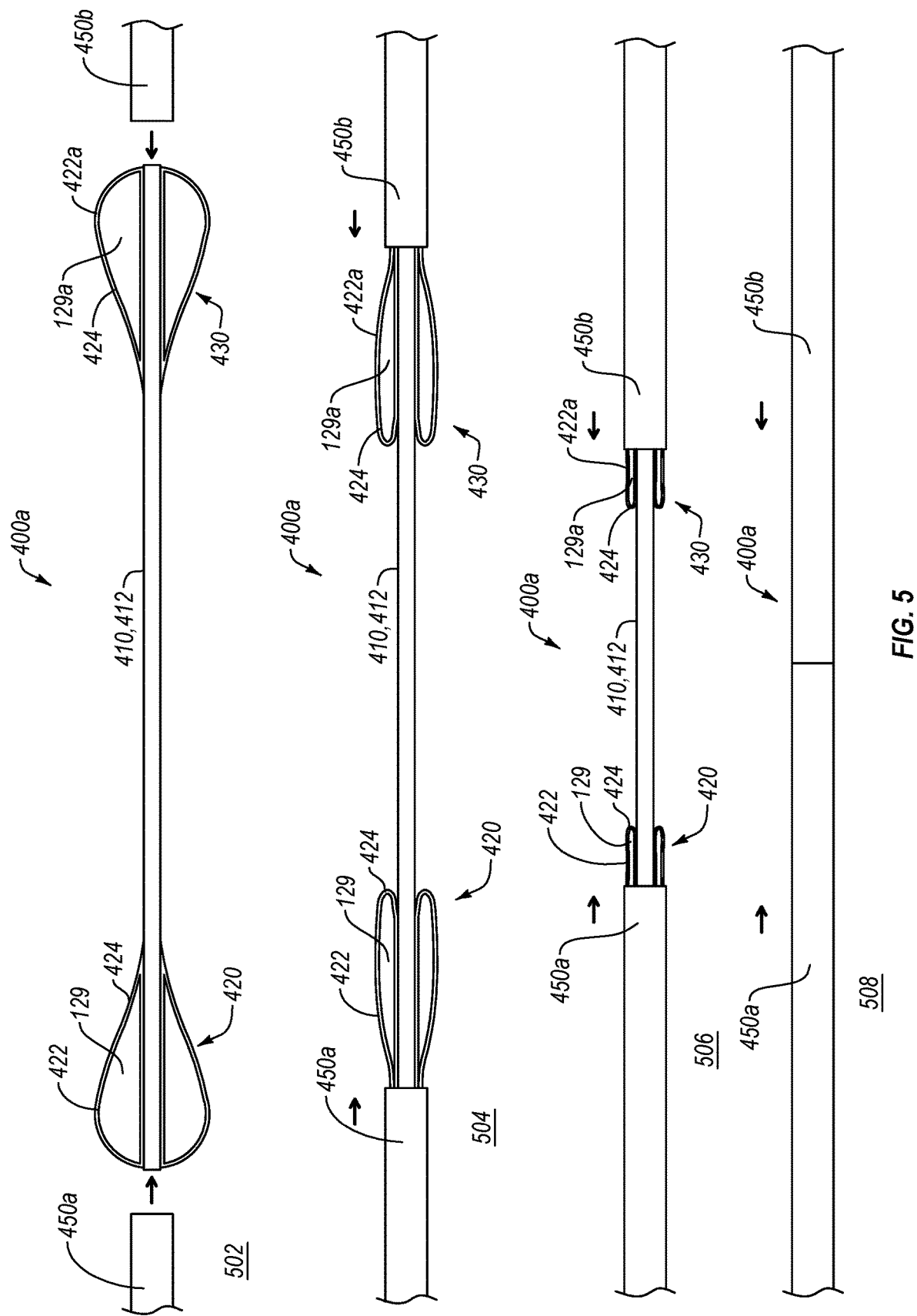
FIG. 5 is a schematic illustration of deformable bladders during placement of a delivery sheath thereover according to an embodiment.

FIG. 5 is a schematic diagram of a method of inserting any of the ureteral stents disclosed herein into a delivery sheath, according to an embodiment. A ureteral stent, such as ureteral stent 400a disclosed above, may be loaded into one or more delivery sheaths 450a and 450b. The delivery sheath 450a and/or 450b may include a hollow cylindrical member having a lumen configured to fit around and enclose at least a portion of the ureteral stent 400a. The delivery sheath(s) 450a and 450b may facilitate delivery of the ureteral stent into a subject (e.g., for urethral insertion). Each delivery sheath 450a and 450b may be positioned about a portion of the ureteral stent 400a by moving the delivery sheath(s) 450a and/or 450b into a concentric position about each end region of the ureteral stent 400a, and moving the delivery sheath(s) 450a and/or 450b axially inward toward a midpoint of the ureteral stent. Responsive to the pressure applied by delivery sheath(s) 450a and/or 450b while it is being positioned about the ureteral stent 400a, the resiliently deformable envelopes 424 and 424a of the deformable bladders 422 and 422a may deform to at least partially comply with the shape of the lumen in the delivery sheath(s) 450a and/or 450b and fit therein.

As shown at stage 502, the ureteral stent 400a includes the deformable bladder 422 at the distal end region 420 and the deformable bladder 422a at the proximal end region 430. The resiliently deformable envelopes 424 and 424a of the respective deformable bladders 422 and 422a may be in a deployed configuration as shown, which may each include a substantially tear-drop shape. The one or more delivery sheaths 450a and/or 450b may be positioned substantially concentrically with the ureteral stent 400a at the distal and proximal end regions 420 and 430, respectively.

As shown at stage 504, as the one or more delivery sheaths 450a and/or 450b are moved longitudinally (e.g., axially) inward on the ureteral stent 400a, the resiliently deformable envelopes 424 and 424a and inert fluids 129 and 129a therein may deform to comply with the pressure exerted thereon by the one or more delivery sheaths 450a and/or 450b. As the one or more delivery sheaths 450a and/or 450b are moved longitudinally inward, the resiliently deformable envelope(s) may elongate along the elongated stent body 410 and the lateral cross-section of the resiliently deformable envelope(s) 424 and 424a may be reduced correspondingly.

As shown at stage 506, as the one or more delivery sheaths 450a and/or 450b are moved progressively longitudinally inward, the resiliently deformable envelope(s) 424 and 424a may be substantially flattened until the lateral cross-section of each of the resiliently deformable envelope(s) 424 and 424a is capable of fitting inside of the delivery sheath, which slides thereover. In such a configuration, the resiliently deformable envelopes 424 and 424a may be maintained in a delivery configuration, and may elastically and reversibly rebound therefrom upon removal of the one or more delivery sheaths 450a and/or 450b. The deformable bladders 422 and/or 422a may rebound to their deployed configuration shape(s) upon removal of the delivery sheaths 450a and 450b and/or may at least partially conform to the anatomical structures therearound.

As shown at stage 508, the one or more delivery sheaths 450a and/or 450b may be advanced inward from the end regions 420 and 430 until substantially all of the deformable bladders 422 and/or 422a or entire ureteral stent 400a is contained therein.

While shown as two portions of delivery sheath closing in from different end regions, in some embodiments, only a single delivery sheath may be positioned over one or more portions of the ureteral stent, such as over the entire ureteral stent. In such embodiments, the delivery sheath may be positioned substantially concentrically with the ureteral stent at an end region thereof, and then advanced over (e.g., concentrically along) the length of the ureteral stent. Such single delivery sheaths may cause at least one deformable bladder associated with the ureteral stent to deform along the elongated stent body, thereby reducing in radial thickness (e.g., lateral cross section) and allowing the elongated stent body to slide into the delivery sheath.

In some embodiments, no delivery sheath is necessary. For example, the resiliently deformable envelopes may be sized and configured to comply and conform to (e.g., fit through) any anatomical structures necessary for proper positioning in a subject. In an embodiment, the resiliently deformable envelope(s) of a ureteral stent may be configured to deform responsive to pressure exerted during insertion into and/or through a urethra, ureter, bladder, and/or kidney. Such a configuration may allow proper positioning of the end regions of the ureteral stent in the kidney and bladder with a lumen thereof in fluid communication between the kidney and bladder.

In an embodiment, the ureteral stents herein may include a device that facilitates retrieval stent from the subject. For example, the distal end region may include a retrieval line attached thereto. The pulling the retrieval line may retrieve the ureteral stent from the subject. In some embodiments, a delivery sheath may slide over the retrieval line to deform the one or more deformable bladders on the ureteral stent sufficient to allow removal of the ureteral stent from the subject.

The ureteral stents herein may be removed by various methods. In an embodiment, a ureteral stent may be removed by pulling on a retrieval line secured to at least one portion of the ureteral stent. In some embodiments, the ureteral stent may be removed, in part, by positioning a delivery sheath thereover (FIG. 5) in situ, such as with the use of a guidewire.

In practice, a guidewire may be inserted into the bladder of the subject and advanced up the ureter of the subject. The position of the guidewire may be monitored via cystoscopy, fluoroscopy or other suitable x-ray imaging technique, or other suitable technique. The assembly of the one or more delivery sheaths 450a and/or 450b enclosing the ureteral stent 400a may be slid over the guidewire that is inserted in the subject, and pushed-up along the guidewire using a suitable pusher device until the proximal end region 430 of the ureteral stent 400a is positioned in the kidney and the distal end region 420 of the ureteral stent 400a is within the bladder of the subject adjacent to the ureter. If the one or more delivery sheaths 450a and/or 450b are employed, the one or more delivery sheaths 450a and/or 450b may include one or more retrieval lines affixed thereto so that the one or more delivery sheaths 450a and/or 450b can be removed from the subject by pulling or retracting the retrieval line(s) after the ureteral stent 400a is properly positioned. After the ureteral stent 400a is properly positioned and if present, the one or more delivery sheaths 450a and/or 450b may be removed by retracting or pulling the retrieval line(s). Removal of the one or more delivery sheaths 450a and/or 450b enables the deformable bladders 422 and/or 422a of the ureteral stent 400a to expand to their deployed configurations. If the one or more delivery sheaths 450a and/or 450b are not employed, the deformable bladders 422 and/or 422a of the ureteral stent 400a may self-deploy after proper positioning thereof. The ureteral stent 400a may be removed, when desired or needed, using another retrieval line attached to the ureteral stent 400a and/or via the same guidewire.

Figure 6:
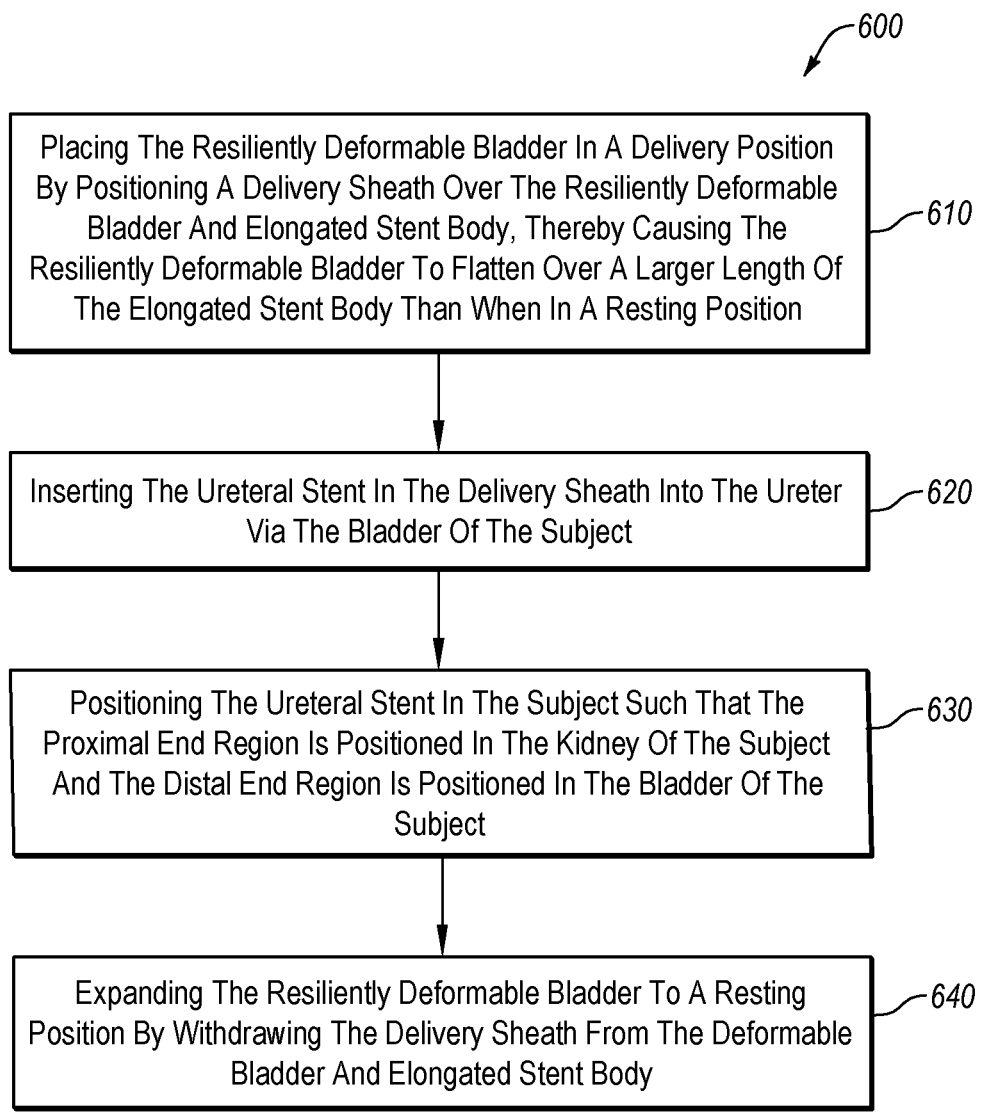
FIG. 6 is a flow chart of a method of deploying a ureteral stent according to an embodiment.

FIG. 6 is a flow chart of a method 600 of deploying a ureteral stent according to an embodiment. The method includes an act 610 of placing the resiliently deformable bladder in a delivery position by positioning a delivery sheath over the resiliently deformable bladder and elongated stent body, thereby causing the resiliently deformable bladder to flatten over a larger length of the elongated stent body than when in a resting position. Placing the resiliently deformable bladder in a delivery position may include deforming one or more deformable bladders positioned around an elongated stent body effective to allow the ureteral stent to fit into one or more anatomical structures of a subject. Deforming the one or more deformable bladders may include placing the deformable bladder(s) in a delivery configuration by positioning the delivery sheath over the deformable bladder(s) and elongated stent body, thereby causing the resiliently deformable bladder to flatten over a larger length of the elongated stent body than when in a deployed configuration. Deforming the one or more deformable bladders may include causing the one or more deformable bladders to elongate along the elongated stent body, and/or off of (e.g., past) an end of the elongated stent body. Causing the one or more deformable bladders to elongate may include correspondingly reducing at least one lateral cross-sectional dimension of the deformable bladders. Deforming the one or more deformable bladders may include sliding at least one delivery sheath over the ureteral stent as disclosed herein. Deforming the one or more deformable bladders may include deforming the bladders with a final amount of inert fluid sealed therein, the final amount of inert fluid being the same amount present in the deployed configuration. In some embodiments, deforming the one more deformable bladders may include deforming a silicone resiliently deformable envelope having mineral oil inert fluid therein.

The method 600 includes an act 620 of inserting the ureteral stent in the delivery sheath, into the ureter via the bladder of the subject. Inserting the ureteral stent into the subject may include inserting the ureteral stent (e.g., in the delivery sheath) into the ureter via the bladder of the subject over a guidewire as previously discussed. Inserting the ureteral stent into a subject may include inserting (e.g., advancing) a proximal end region of the ureteral stent into the kidney of the subject, such as via the ureter of the subject. Inserting the ureteral stent into the subject may include inserting one or more deformable bladders with a final amount of inert fluid sealed therein, the final amount of inert fluid being the same amount present in the deployed configuration.

The method 600 includes an act 630 of positioning the ureteral stent in the subject such that the proximal end region is positioned in the kidney of the subject and the distal end region is positioned in the bladder of the subject. In an embodiment, positioning the proximal end region of the ureteral stent in the kidney of the subject may include positioning a first retaining structure (e.g., coil or deformable bladder) in the kidney of the subject, such as at or adjacent to a ureteral orifice in the kidney of the subject. In an embodiment, positioning the ureteral stent into a subject may include positioning a distal end region of the ureteral stent in the bladder of the subject. In an embodiment, positioning a distal end region of the ureteral stent in the bladder of the subject may include positioning the deformable bladder at the distal end region at or adjacent to the trigone and/or at or adjacent to the ureteral orifice in the bladder of the subject.

The method 600 includes an act 640 of expanding the deformable bladder to a deployed position. Expanding the deformable bladder to a deployed position may include expanding one or more deformable bladders to a deployed position such as a deformable bladder at each of the proximal and distal end regions. Expanding the deformable bladder to a deployed position may be accomplished by withdrawing the delivery sheath from the deformable bladder and elongated stent body. Withdrawing the delivery sheath from the deformable bladder and elongated stent body may include withdrawing (e.g., pulling) a retrieval line attached to the delivery sheath or via a guidewire.

The ureteral stent of the method 600 can include using any of the ureteral stents disclosed herein. In some embodiments, the method 600 may include providing a ureteral stent. Providing a ureteral stent can include providing any of the ureteral stents disclosed herein. For example, providing a ureteral stent can include providing a ureteral stent having an elongated stent body including a proximal end region including a first retaining structure (e.g., deformable bladder, pig-tail, etc.), a distal end region spaced longitudinally from the proximal end region, an outer surface, an inner surface defining a lumen extending between the proximal end region and the distal end region of the elongated stent body; and a deformable bladder secured to and surrounding at least a portion of the distal end region of the elongated stent body, the deformable bladder having a resiliently deformable envelope that is imperforately sealed and having an inert fluid therein.

In some embodiments, one or more of the above acts may be omitted. For example, placing the deformable bladder(s) in a delivery position by positioning a delivery sheath over the deformable bladder(s) and elongated stent body may be omitted and the ureteral stent may be inserted into a patient without a delivery sheath via a guidewire. In such an embodiment, the deformable bladders may be deformed responsive to pressure from the anatomic structures of the subject during insertion.

In an embodiment, the method 600 may include using a guidewire to position the ureteral stent in the subject. Using a guidewire may include inserting an advancing tip of a guidewire into and through the bladder, into and through the ureter of the subject, and into the kidney of the subject. Using a guidewire may include positioning the ureteral stent on the guidewire, such as by placing an end portion of the guidewire within the lumen of the ureteral stent. Using a guidewire may include advancing the ureteral stent along the guidewire until the proximal end region of the ureteral stent is positioned in the kidney and the distal end region of the ureteral stent is within the bladder of the subject adjacent to the ureter (e.g., at the ureteral orifice and/or trigone). After the ureteral stent is positioned in the ureter, the user may remove the guidewire from the subject.

In embodiment, responsive to a subject's anatomy and/or medical condition, a user (e.g., medical professional) may select an appropriately sized and configured ureteral stent. Selecting an appropriately sized ureteral stent may include selecting one or more of elongated body length and/or width (e.g., diameter), deformable bladder and/or first retaining structure type or shape, deformable bladder and/or first retaining longitudinal length, deformable bladder and/or first retaining structure lateral dimension(s), material type(s), any other criteria disclosed herein, or combinations of any of the foregoing.

Any of the embodiments disclosed herein may include an anti-bacterial coating applied to at least a portion of the ureteral stent. For example, one or more of the elongated stent body (e.g., the inner and/or outer surface of the at least one sidewall), the deformable bladder, or the first retaining structure may have the first coating applied thereto. In an embodiment, the anti-bacterial coating may include a metal, such as gold, palladium, silver, alloys thereof, and combinations thereof. Compared to an uncoated stent, the anti-bacterial coating may reduce the likelihood of infection caused by the ureteral stent. The anti-bacterial coating may be applied to a ureteral stent configured to be used during an extended period. In an embodiment, the anti-bacterial coating may include ions and/or molecules composted to be released by the anti-bacterial coating into the surrounding environment. The ions and/or molecules may be composed, for example, to decrease the likelihood of infection caused by the ureteral stent. In an embodiment, the anti-bacterial coating may be configuring to not interfere with the operation of one or more components of the ureteral stent. For example, the anti-bacterial coating may be configured not inhibit selective closure of the lumen to prevent reflux.

The anti-bacterial coating may have an additional coating applied thereto. In an embodiment, the additional coating may be configured to protect the first coating. For example, the additional coating may include a hydrogel. In another embodiment, the additional coating may transport the ions and/or molecules from the first coating into the surrounding environment.

While various aspects and embodiments have been disclosed herein, other aspects and embodiments are contemplated. The various aspects and embodiments disclosed herein are for purposes of illustration and are not intended to be limiting.

What is claimed is:

1. A ureteral stent, comprising:
an elongated stent body including:
   a proximal end region including a first retaining structure, the proximal end region configured for positioning in a kidney;
   a distal end region configured for positioning in a bladder and spaced longitudinally from the proximal end region;
   an outer surface; and
   an inner surface defining a lumen extending between the proximal end region and the distal end region of the elongated stent body; and
a deformable bladder secured to and surrounding at least a portion of the distal end region of the elongated stent body, the deformable bladder including:
   a resiliently deformable imperforate envelope; and
   an inert fluid imperforately sealed within the resiliently deformable imperforate envelope.

2. The ureteral stent of claim 1, wherein the resiliently deformable envelope is formed from a material having a modulus of elasticity and dimensions effective to allow the deformable bladder to elongate along a portion of the outer surface of the elongated stent body and reduce the at least one cross-sectional dimension responsive to an external pressure applied thereto.

3. The ureteral stent of claim 1, wherein:
the elongated stent body includes one or more of a perforated portion, a discontinuity, a portion having a thinner construction than adjacent portions of the elongated stent body, or a portion made with a different and more collapsible material than surrounding portions of the elongated stent body; and
the perforated portion, the discontinuity, the portion having the thinner construction, or the portion made with the different and more collapsible material is configured to collapse and substantially close the lumen responsive to external pressure from the bladder during urination.

4. The ureteral stent of claim 1, wherein the resiliently deformable imperforate envelope includes an elastomer having one or more of silicone rubber, natural rubber, natural polyisoprene, polyurethane, synthetic polyisoprene nylon, or nitrile.

5. The ureteral stent of claim 1, wherein the inert fluid includes one or more of mineral oil, cold-pressed vegetable oil, coconut oil, almond oil, olive oil, or a seed oil.

6. The ureteral stent of claim 1, wherein the resiliently deformable imperforate envelope, including the inert fluid therein, is sized and configured to deform and fit inside of a delivery sheath suitable for insertion into a ureter of a subject.

7. The ureteral stent of claim 6, further comprising the delivery sheath, the delivery sheath configured to fit over a length of the ureteral stent and cause the resiliently deformable imperforate envelope to at least partially deform and fit therein.

8. The ureteral stent of claim 1, wherein the deformable bladder has a substantially teardrop deployed shape.

9. The ureteral stent of claim 1, wherein the resiliently deformable imperforate envelope has a first portion and a second portion, the first portion having a greater wall thickness than the second portion.

10. The ureteral stent of claim 9, wherein the elongated stent body includes a collapsible portion, the collapsible portion including one or more of a perforated portion, a discontinuity, a portion having a thinner construction than adjacent portions of the elongated stent body, or a portion made with a different, a more collapsible material than sidewall material in surrounding portions of the elongated stent body;
    wherein each of the perforated portion, the discontinuity, the portion having a thinner construction, or the portion made with the different, more collapsible material is configured to collapse and substantially close the lumen of the elongated stent body responsive to external pressure from the bladder during urination; and
    wherein the second portion of the resiliently deformable envelope is positioned proximate to the collapsible portion of the elongated stent body when the resiliently deformable envelope is in a deployed configuration.

11. The ureteral stent of claim 1, wherein the first retaining structure includes an additional deformable bladder, the additional deformable bladder including:
    an additional resiliently deformable envelope that is imperforately sealed; and
    an additional inert fluid disposed in the additional resiliently deformable envelope;
    wherein the additional resiliently deformable envelope is configured to allow the additional deformable bladder to elongate along a portion of the outer surface of the elongated stent body and reduce at least one cross-sectional dimension of the additional resiliently deformable envelope responsive to external pressure applied thereto.

12. The ureteral stent of claim 11, wherein the additional resiliently deformable envelope includes an elastomer having one or more of silicone rubber, natural rubber, natural polyisoprene, synthetic polyisoprene polyurethane, nylon, or nitrile.

13. The ureteral stent of claim 11, wherein the additional inert fluid includes one or more of mineral oil, cold-pressed vegetable oil, coconut oil, almond oil, olive oil, or a seed oil.

14. The ureteral stent of claim 11, wherein the additional deformable bladder is configured identically to the deformable bladder.

15. The ureteral stent of claim 1, wherein the elongated stent body is coated with at least one material selected from gold, palladium, and silver.

16. The urethral stent of claim 1, wherein the elongated stent body and the deformable bladder have no filling port or valve.

\* \* \* \* \*